(12) United States Patent
Antonini (10) Patent No.: US 7,671,203 B2
(45) Date of Patent: Mar. 2, 2010

(54) METHOD AND SYSTEM FOR SEPARATION AND PURIFICATION OF AT LEAST ONE NARCOTIC ALKALOID USING REVERSE PHASE PREPARATIVE CHROMATOGRAPHY

(75) Inventor: Enrico Anthony Antonini, Edwardsville, IL (US)

(73) Assignee: Mallinckrodt Inc., Hazelwood, MO (US)

( * ) Notice: Subject to any disclaimer, the term of this patent is extended or adjusted under 35 U.S.C. 154(b) by 619 days.

(21) Appl. No.: 10/501,353

(22) PCT Filed: Feb. 18, 2003

(86) PCT No.: PCT/US03/04498

§ 371 (c)(1), (2), (4) Date: Jul. 14, 2004

(87) PCT Pub. No.: WO03/074526

PCT Pub. Date: Sep. 12, 2003

(65) Prior Publication Data

US 2005/0182257 A1    Aug. 18, 2005

(51) Int. Cl.
C07D 489/02    (2006.01)

(52) U.S. Cl. ...................................................... 546/44

(58) Field of Classification Search .................... 546/44
See application file for complete search history.

(56) References Cited

U.S. PATENT DOCUMENTS

| 4,189,583 | A | 2/1980 | Gless et al. |
|---|---|---|---|
| 4,198,344 | A | 4/1980 | Ferrari |
| 4,277,604 | A | 7/1981 | Dauben et al. |
| 4,514,569 | A | 4/1985 | Hendrickson et al. |
| 4,597,866 | A | 7/1986 | Couillard |
| 4,764,615 | A | 8/1988 | Ayyangar et al. |
| 4,769,452 | A | 9/1988 | Boulware |
| 4,798,792 | A | 1/1989 | Harder et al. |
| 4,831,133 | A | 5/1989 | Goodbody et al. |
| 4,956,429 | A | 9/1990 | Harmetz et al. |
| 5,039,804 | A | 8/1991 | Brackeen et al. |
| 5,119,835 | A | 6/1992 | Ehling et al. |
| 5,133,981 | A | 7/1992 | Harkrader et al. |
| 5,158,676 | A | 10/1992 | Kreher et al. |
| 5,167,809 | A | 12/1992 | Mann et al. |
| 5,176,913 | A | 1/1993 | Honerlagen et al. |
| 5,196,351 | A | 3/1993 | Harris et al. |
| 5,230,802 | A | 7/1993 | Ferguson et al. |
| 5,352,789 | A | 10/1994 | Hinz |
| 5,504,208 | A | 4/1996 | Bulej et al. |
| 5,527,913 | A | 6/1996 | Hinz |
| 5,534,620 | A | 7/1996 | Kearns et al. |
| 5,571,685 | A | 11/1996 | Bruce |
| 5,578,725 | A | 11/1996 | Portoghese et al. |
| 5,608,066 | A | 3/1997 | Hinz |
| 5,667,675 | A | 9/1997 | Hatch et al. |
| 5,723,625 | A | 3/1998 | Keplinger et al. |
| 5,906,848 | A | 5/1999 | Kreuter et al. |
| 5,981,750 | A | 11/1999 | Corcoran et al. |
| 6,001,260 | A | 12/1999 | Hatch et al. |
| 6,015,903 | A | 1/2000 | Brase et al. |
| 6,024,998 | A | 2/2000 | Kreuter et al. |
| 6,054,584 | A | 4/2000 | Ma et al. |
| 6,054,585 | A | 4/2000 | Badmaev et al. |
| 6,067,749 | A | 5/2000 | Fist et al. |
| 6,090,943 | A | 7/2000 | Dung et al. |
| 6,218,541 | B1 | 4/2001 | Wang |
| 6,224,847 | B1 | 5/2001 | Noakes et al. |
| 6,235,906 | B1 | 5/2001 | Sebastian |
| 6,265,542 | B1 | 7/2001 | Fahrner et al. |
| 6,376,221 | B1 | 4/2002 | Fist et al. |
| 2002/0042429 | A1 | 4/2002 | Myers et al. |
| 2003/0087306 | A1 | 5/2003 | Christensen et al. |

FOREIGN PATENT DOCUMENTS

| AU | 9873939 | 1/1999 |
|---|---|---|
| AU | 9920414 | 8/1999 |
| AU | 725396 | 10/2000 |
| CA | 2241772 | 12/1998 |
| DE | 19743176 | 4/1999 |
| EP | 0022418 | 1/1981 |
| EP | 889045 | 1/1999 |
| GB | 773467 | 4/1957 |
| GB | 890614 | 3/1962 |
| JP | 11071375 | 3/1999 |
| JP | 02001122869 A | 9/2000 |

(Continued)

OTHER PUBLICATIONS

Vandenberghe, H. et al.: Analysis of morphine in serum by high performance liquid chromatography with amperometric detection. Therap. Drug Monit., vol. 4, pp. 307-314, 1982.*

Matantseva, E.F. et al.: Quantitative determination of opium alkaloids by liquid chromatography methods. Khimiya Prirodnykh Soedinenii, vol. 5, pp. 730-731, 1980 ( see enclosed english translation ).*

Proksa, B.; Separation of Products of Thebaine Rearrangement by Capillary Electrophoresis in the Presence of Cyclodextrins, Slovakofarma a.s., Hlohovec, Slovakia. Chem Pap. (2001), 55(3), 196-201. CODEN: CHPAEG ISSN: 0366-6352. Journal written in English. AN 2001:656754 CAPLUS (Copyright 2001 ACS).

Maeda, Dean Y.; Coop, Andres; An Improved Hydrolysis of 7α-chloro-7β-cyano-6,14-endoethenotetrahydrothebaine to its 7-oxo derivative; University of Maryland School of Pharmacy, Baltimore, MD, USA. Heterocycles (2001), 55(6), 1147-1149. CODEN: HTCYAM ISSN: 0385-5414. Journal written in English. CAN 135: 166948 AN2001:430551 CAPLUS (Copyright 2001 ACS).

(Continued)

Primary Examiner—Charanjit S Aulakh (57) ABSTRACT

An apparatus and method for separating at least one narcotic alkaloid that includes loading a stationary phase media into a high performance preparative liquid chromatography column, feeding a crude narcotic alkaloid solution into the chromatographic column, applying a mobile phase to the chromatographic column, and recovering a narcotic alkaloid eluate from the chromatographic column. The narcotic eluates are collected and treated separately from each other. Each separated alkaloid, however, has sufficient recovery and purity.

49 Claims, 3 Drawing Sheets

FOREIGN PATENT DOCUMENTS

| WO | WO9935902 | 7/1990 |
| WO | WO9400565 | 1/1994 |
| WO | WO9526794 | 10/1995 |
| WO | WO98/02033 | 1/1998 |
| WO | WO9916526 | 4/1999 |
| WO | WO0058333 | 10/2000 |

OTHER PUBLICATIONS

Facchini, Peter J.; Park, Sang-Un; Bird, David A.; Samanani, Nailish; Toward the Metabolic Engineering of Benzylisoquinoline Alkaloid Biosynthesis In Opium Poppy and Related Species; Department of Biological Sciences University of Calgary, Calgary AB, Can. Recent Res. Dev. Phytochem (200), 4 31-47. CODEN: RDPHF5 Journal written in English. AN 2001:766123 CAPLUS (Copyrigvht 2001 ACS).

Then, Maria; Illes, Vendel; Daood, Hussein; Szalai, Otto; Vetalan, Lorant; Szentmihalyi, Klara; Vegyipari Muveletek Tanszek, Extraction of Poppy Plants and Mixtures of Different Drug Plants With Poppy-Seed by Mans of Supercritical and Soxhlet Methods; Extraction of poppy plants of different maturity and that of 40-60 proportion mixtures of garden sage, camomile flower and marigold with poppy-seed has been studied in a flow through extraction equipment at 35 C and 250 and 300 bar pressures using CO2 solvent as well as in con-ventional (Soxhlet) e, Veszprem, Hung. Olaj, Szappan, Kozmet. (2000), 49 (Kulonszam), 33-39, CODEN: OSZKAT ISSN: 0472-8602. Journal written in Hungarian CAN 134-61317 AN2000:713713 CAPLUS (Copyright 2001 ACS).

Bruce, Neil C.; Engineering Novel Biocatalytic Routes for Production of Semisynthetic Opiate Drugs; Institute of Biotechnology, University of Cambridge, Cambridge, UK. Book of Abstracts 219th ACS National Meting, San Francisco, CA Mar. 26-30, 1000 (2000), BIOT-007; Publisher: American Chemical Society, Washington, D.C. CODEN: 69CLAC Conference; meeting abastract written in English; AN200:327226 CAPLUS (Copyright 2001 ACS).

Votruba, Jaroslav, Fleiger, Miroslav; Separat of Ergot Alkaloids by Adsorptoin of Silicates; Institute of Microbiology, Academy of Sciences of the Czech Republic, Prague, Czech Rep. Biotechnol. Lett. (2000), 22(16), 1281-1285 CODEN:BILED3 ISSN: 0141-5492 Journal written in English CAN 133:361926 AN 2000:722947 CAPLUS (Copyright 2001 ACS).

Navratil, O.; Skalican, Z.; Kobliha, Z.; Halamek, E.; Extraction of Selected Organic Bases by bis 1,2-dicarbollylcobaltate Anion From Water Into Chloroform; Department of Chemistry, Military University, Vyskov, Czech Rep. Czech J. Phys. (1999), 49 (Suppl. 1, Pt. 2, 13th Radiochemical Conference 1998) 731-738 CODEN: CZYPAO ISSN: 0011-4626, Journal wirtten in English CAN 131:175697 AN 1999:410423 CAPLUS (Copyright 2001 ACS).

R.G. Peterson, et al., Amperometric high-performance liquid chromatographic method for narcotic alkaloids, Journal of Chromatography, 1980, vol. 188, p. 420-425.

I. Lewandowska et al., Chromatogtaphic separation and seterminartion of alkaloids in the Pantopon type drugs, Chemical Abstracts, 1968, vol. 68, No. 28.

Lihong Gu, The detection of the contents of Morphine and Codeine in the pericarpium papaveris by Reverse phase HPLC, Guangdong Pharmaceutical Journal, vol. 9, No. 3, pp. 17-18, 1999.

Hao Hongyan et al., Determination of 3 bio-active alkaloids in the Chinese drug pericarpium papaveris by HPLC and HPCE, 2000, Acta Pharmaceutica Sinica, 35(4), pp. 289-293.

Lihong Gu, Antiphaase HPLC Determination Morphine, Codeine Content in Pericarpium Papaveris, Fast-Trans Translation, GLTaC, Inc., pp. 1-4.

* cited by examiner

Fig-2.

METHOD AND SYSTEM FOR SEPARATION AND PURIFICATION OF AT LEAST ONE NARCOTIC ALKALOID USING REVERSE PHASE PREPARATIVE CHROMATOGRAPHY

CROSS REFERENCE TO RELATED APPLICATIONS

This is a national stage application of PCT/US03/04498, filed Feb. 18, 2003, which claims the benefit of U.S. Provisional Patent Application No. 60/360,321, filed Feb. 28, 2002.

FIELD OF THE INVENTION

This invention relates to a method and system for industrial separation and purification of at least one narcotic alkaloid, and more particularly, to a method and system for the separation and purification of at least one narcotic alkaloid using reverse phase preparative chromatography.

BACKGROUND OF THE INVENTION

Heretofore, the most common process to separate narcotic alkaloids, which includes morphine, codeine, oripavine, thebaine, papaverine and narcotine (noscapine), is by solvent extraction. Separation includes both purification as well as color removal. The separated narcotic alkaloids are then purified by carbon adsorption and precipitation. Unfortunately, the carbon irreversibly adsorbs alkaloids of interest in addition to removing color and other unwanted substances. This creates a significant yield loss. Moreover, a yield loss will also occur in the supernatant in the alkaloid isolations. A solvent, such as ethanol, is typically required to promote purity in the precipitate. However, these solvent additions often cause yield loss in the supernatant that are not fully recovered. In some instances, multiple precipitations are required in order to achieve the desired purity. This greatly increases the complexity of the process since the supernatant streams must be recycled for recovery. These additional precipitations also require using a greater volume of raw narcotic alkaloids in the process with longer cycle times. Furthermore, the precipitation process can be lengthy in addition to the time that is sometimes required for heating and cooling. Also, some precipitations require extended filtration time due to the particle size of the narcotic alkaloid that is eventually produced.

Other drawbacks to the current process of purifying narcotic alkaloids with solvent extraction, adsorption and precipitation include a multiple of manual solid handling operations to recover the narcotic alkaloid. These operations lead to greater operator exposure to narcotics with the associated reliance on engineering controls and personal protective equipment. This operation can be monotonous as well as tedious.

Although there have been modifications to the precipitation process to improve both the solvent extraction and alkaloid precipitations, there are still limitations since the separation process requires significantly different solubility. Improving the purity after precipitation often reduces yield in the supernatant.

One specific example of this type of modified solvent extraction is found in U.S. Pat. No. 6,054,584 issued to Ma, et al. on Apr. 25, 2000, which discloses a process for extracting only morphine from opium where the opium is dissolved in a basic alcoholic solution. The basic alcoholic solution is then filtered and the alcohol is removed from the filtrate to leave a residue. The residue is then extracted with a basic aqueous solution having a pH of at least 11. The basic aqueous solution may be filtered to remove any solid matter remaining after the aqueous extraction step, and then is stirred with a sufficient amount of salt to avoid the formation of an emulsion. The basic aqueous solution or filtrate is then extracted with benzene or toluene. Next, the pH of the basic aqueous filtrate is adjusted to a pH of between 8.5 to 9.5, which allows the morphine to precipitate for recovery.

There are a number of different ways to achieve adsorption besides the use of carbon. One way to achieve adsorption is through ion exchange. Although this was done with both codeine and morphine, it has the limitation of requiring a low feed concentration. This is due to the need of using high pH flushes, which can cause precipitation. Any precipitation can potentially compromise the entire purification process. Another disadvantage to this approach is that significant salt is required so that another step of either dialysis or reverse osmosis is required for ion-removal.

Yet another way to achieve adsorption is through polar interaction or normal phase adsorption. Although this method is successful, it requires the extensive use of organic solvents. Moreover, although the alkaloids can be separated from each other, more evaporation is required.

Still another way to achieve adsorption is through separating alkaloids from other components based on molecular size by utilizing a membrane. This purification method is limited to either removing larger or smaller components. There is a yield loss due to the inherent imperfections in the membrane.

Any use of analytical chromatography on narcotic alkaloids would teach an individual of ordinary skill in the art away from using preparative chromatography. Unlike preparative chromatography, analytical chromatography generally requires complete separation of each peak, as measured by ultraviolet absorbance. This is achieved by loading an infinitely small mass of the feed onto the column, and using a small particle size diameter (often less than 5 micrometers (196.85 microinches)) in the stationary phase. The small particle size generates much higher pressures than those found in preparative chromatography. These higher pressures mandate the use of very large, strong and expensive chromatography equipment, which would negate the commercial viability for this analytical process. The equipment would also be very large in consideration that an infinitely small mass of feed is loaded in each run. In preparative chromatography, the objective is to recover the desired feed component with the required purity. The desired component can be recovered with impurities, so long as the impurities are within specification limits. The particle size of the stationary phase is small enough to achieve the separation, but is often greater than 10 micrometers (393.70 microinches). This limits the pressure drop generated. Also, in preparative chromatography, the maximum amount of feed is loaded with the constraint of attaining the desired product quality. This allows the product to leave the column with a maximum concentration, which then minimizes the size of the downstream equipment, especially any evaporating or concentrating units.

Any use of analytical chromatography on narcotic alkaloids would teach an individual of ordinary skill in the art away from using preparative chromatography. Unlike preparative chromatography, analytical chromatography generally requires peak separation, as measured by ultraviolet absorbance, since it makes it extremely difficult to determine when the different narcotic alkaloids are eluting from the chromatography column. Moreover, in direct contrast to preparative chromatography, analytical chromatography generally prohibits the elution of impurities with each product having a separate peak. Likewise, the loading ratio utilized with analytical chromatography equipment along with the small particle size of the expensive stationary phase media generates much higher pressures than those found in preparative chromatography. These higher pressures mandate the use of very large, strong and expensive chromatography equipment, which would negate the commercial viability for this analytical process. The present invention is directed to overcoming one or more of the problems set forth above. These deficiencies and shortcomings include, but are not limited to, narcotic alkaloid yield loss, tedious manual solid handling operations such as the loading and unloading of centrifuges or filters, reliance on protective equipment by the operator, extensive processing steps and potential multiple precipitations in order to achieve the requisite purity requirements.

SUMMARY OF INVENTION

In one aspect of this invention, a method for separating at least one narcotic alkaloid using preparative chromatography is disclosed. This method includes loading a stationary phase media into a chromatographic column, feeding a crude narcotic alkaloid solution into the chromatographic column, applying at least one mobile phase to the chromatographic column, and recovering at least one narcotic alkaloid eluate from the chromatographic column.

In another aspect of this invention, a method for separating at least one narcotic alkaloid using preparative chromatography is disclosed. This method includes feeding a crude narcotic alkaloid solution into a chromatographic column that includes stationary phase media. This is followed by applying a series of mobile phases, e.g., three (3), to the chromatographic column. The first mobile phase is an acidic solution, the acidic solution has a pH that is in a range from about 2 to about 5. This allows the recovery of three (3) narcotic alkaloid eluates from the chromatographic column, which includes morphine, codeine and oripavine in sequence. The second mobile phase applied to the chromatographic column is a first solvent, wherein the first solvent has a pH that is in a range from about 2 to about 5. This provides for a recovery of a thebaine eluate from the chromatographic column. The third mobile phase applied to the chromatographic column is a second solvent and the second solvent has a pH that is in a range from about 2 to about 5. This provides for a recovery of a narcotine eluate and a papaverine eluate from the chromatographic column.

In yet another aspect of this invention, a system for separating at least one narcotic alkaloid using preparative chromatography is disclosed. This system includes a preparative chromatographic column that may conveniently have a diameter that is at least 5 centimeters (1.97 inches) for increased throughput and having an inlet and an outlet. This system also includes a piston, having a plate with an upper face and a lower face, and a rod attached to the upper face of the plate. Within the chromatographic column, there is a hydraulic fluid chamber located above the upper face of the plate and a media chamber located below the lower face of the plate. The plate provides separation between the hydraulic fluid chamber and the media chamber. There is a fluid pressure applying mechanism for providing fluid to the hydraulic fluid chamber for moving the plate of the piston downward and compressing a stationary phase media in the media chamber. Crude narcotic alkaloid solution is then received from the inlet followed by at least one mobile phase that is also received by the inlet of the chromatographic column, wherein at least one narcotic alkaloid is then eluted from the outlet of the chromatographic column.

In still another aspect of this invention, a system for separating at least one narcotic alkaloid using preparative chromatography is disclosed. This system includes a chromatographic column with a diameter that may conveniently be at least 5 centimeters (1.97 inches) and having an inlet and an outlet. This system also includes a piston, having a plate with an upper face and a lower face, and a rod attached to the upper face of the plate. Within the chromatographic column, there is a hydraulic fluid chamber located above the upper face of the plate and a media chamber located below the lower face of the plate. There is a fluid pressure applying mechanism for providing fluid to the hydraulic fluid chamber for moving the plate of the piston downward and compressing a stationary phase media in the media chamber. Crude narcotic alkaloid solution is then received by the inlet followed by at least one mobile phase that is also received by the inlet of the chromatographic column, wherein at least one narcotic alkaloid is then eluted from the outlet of the chromatographic column. There is at least one valve mechanism that provides a flow of the stationary phase media into the inlet of chromatographic column and then removes fluid during the compression of the stationary phase media, wherein the at least one valve mechanism, after compression of the stationary phase media, then provides a flow of a crude narcotic alkaloid solution into the inlet of the chromatographic column followed by a flow of at least one mobile phase. The at least one valve mechanism then allows at least one narcotic alkaloid to elute from the outlet of the chromatographic column.

These are merely a few illustrative aspects of the present invention and should not be deemed an all-inclusive listing of the innumerable aspects associated with the present invention. These and other aspects will become apparent to those skilled in the art in light of the following disclosure and accompanying drawings.

BRIEF DESCRIPTION OF DRAWINGS

For a better understanding of the present invention, reference may be made to the accompanying drawings in which.

DETAILED DESCRIPTION OF THE INVENTION

Figure 1:
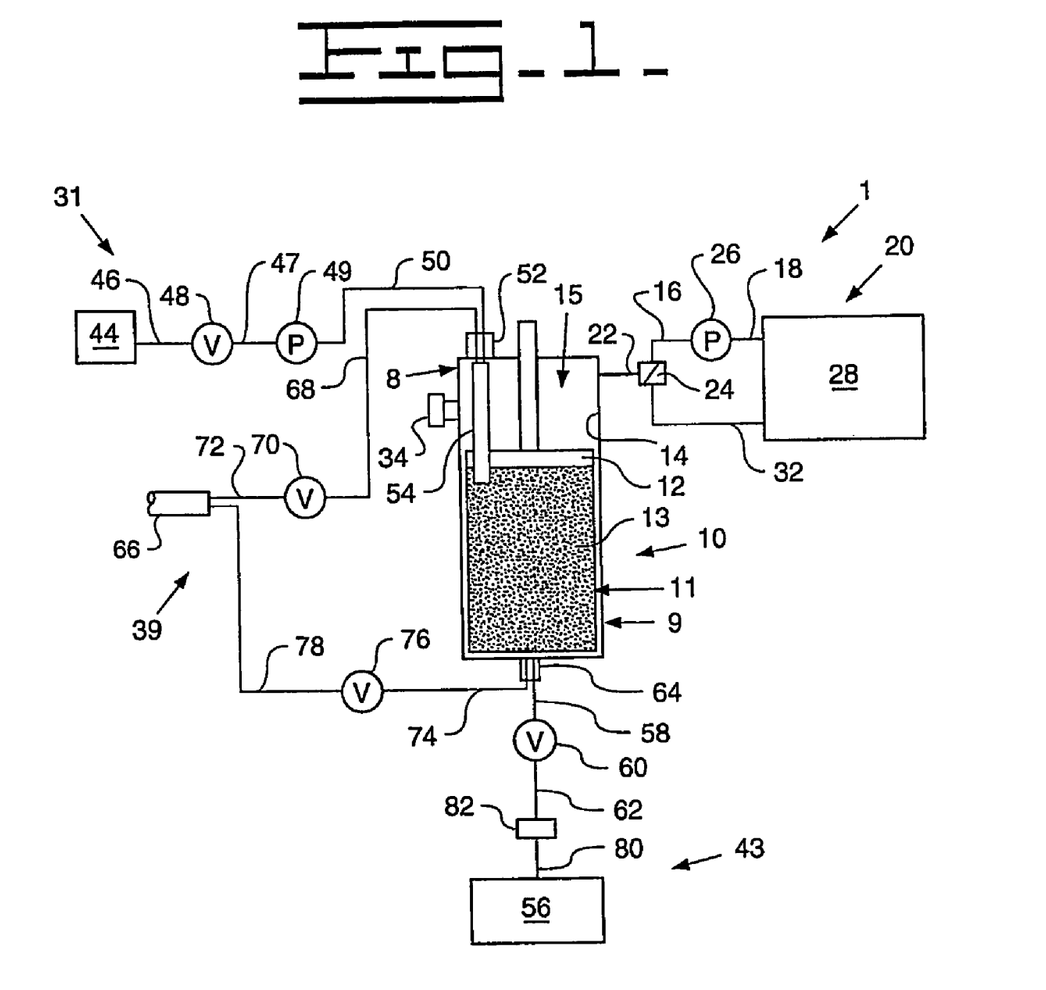
FIG. 1 is a schematic diagram of a system of the present invention for recovering a narcotic eluate from a crude alkaloid solution including a preparative chromatography column, a hydraulic fluid pressure applying mechanism, a liquid applying mechanism, a fluid purge mechanism and an eluate receiving mechanism.

Referring now to FIG. 1, a schematic diagram of a system of the present invention for recovering a narcotic eluate from a crude alkaloid solution is generally indicated by numeral 1. A high performance preparative liquid chromatography column (HPLC) is generally indicated by numeral 10, having a top portion 8 and a bottom portion 9. The preparative chromatography column 10, in an exemplary preferred system, includes a diameter that is at least about 5 centimeters (1.97 inches). The length of the preparative chromatography column 10 is not critical to the process with a preferred length that ranges from about 5 centimeters (1.97 inches) to about 100 centimeters (39.4 inches) with a more preferred length that ranges from about 20 centimeters (7.87 inches) to about 30 centimeters (11.81 inches). There are a variety of commercial suppliers that can build preparative chromatography columns of this nature including Amicon, Inc., having a place of business at 72 Cherry Hill Drive, Beverly, Mass. 01915. Amicon, Inc. is the manufacturer of PROCHROM® chromatography columns. Other manufacturers include TechniKrom, Incorporated, having a place of business at 1801 Maple Avenue, Evanston, Ill. 60201, among others. The present invention is applicable to a wide variety of high performance liquid preparative chromatography columns and is not limited to the specific embodiment detailed in this patent application.

There is a piston 12 that can move up and down inside the preparative chromatography column 10. The piston 12 divides the preparative chromatography column 10 into two dynamic chambers. There is a media chamber 11 located below the piston 12 and a hydraulic fluid chamber 15 located above the piston 12. The outer circumference of the piston 12 functions as a seal against the inside wall 14 of the preparative chromatography column 10. The movement of the piston 12 in the preparative chromatography column 10 is through the application of hydraulic fluid, e.g., food grade oil, supplied from a hydraulic fluid pressure applying mechanism 20.

Hydraulic fluid pressure is supplied through a first hydraulic conduit 16 that is connected to a hydraulic switch 24, which is in fluid communication with the hydraulic fluid chamber 15 through a hydraulic fluid conduit 22. The other end of the first hydraulic conduit 16 is connected to a hydraulic pump 26. The hydraulic pump 26 receives fluid from a hydraulic reservoir 28 through a second hydraulic conduit 18. The hydraulic switch 24 allows the hydraulic fluid to flow from the hydraulic reservoir 28 under pressure from the hydraulic pump 26 and through the hydraulic fluid conduit 22 and into the hydraulic fluid chamber 15 to move the piston 12 downward. When the hydraulic switch 24 is flipped in the opposite direction, hydraulic fluid is diverted through a third hydraulic conduit 32 and back into the hydraulic reservoir 28.

There is a liquid applying mechanism 31 for providing: a) at least one media flushing solution; b) a crude alkaloid solution; and c) at least one mobile phase to the preparative chromatography column 10. In the preferred embodiment, there are at least one (1) media flushing solution and three (3) mobile phases. However, a separate liquid applying mechanism 31 may be utilized for each individual solution or mobile phase provided to the preparative chromatography column 10. The liquid applying mechanism 31 includes a liquid tank 44 for providing a liquid to the preparative chromatography column 10 through a first liquid conduit 46 that is connected in a fluid relationship to a first liquid valve 48, which controls the flow of liquid from the liquid tank 44. The other end of the first liquid valve 48 is connected to a second liquid conduit 47 that is connected in fluid relationship to a liquid pump 49. The liquid pump 49 is connected to a third liquid conduit 50 that is in fluid relationship to a fluid inlet 52 for the preparative chromatography column 10. A nonlimiting, illustrative example of a liquid pump 49 is a VARIAN® Prepstar™ pump. VARIAN is a federally registered trademark of Varian, Inc., having a place of business at 3120 Hansen Way, Palo Alto, Calif. 94304-1030. The fluid from the fluid inlet 52 is directed by an internal conduit 54 so that that liquid flows directly below the piston 12 into the media chamber 11 of the preparative chromatography column 10.

There is also an eluate receiving mechanism 43 that includes an eluate tank 56 for receiving eluted narcotic alkaloids from the preparative chromatography column 10 through a sixth liquid conduit 80 that is connected in fluid relationship to an eluate detection device 82. An illustrative, but nonlimiting, example of an eluate detection device 82 that can detect specific narcotic alkaloids as they are being eluted from the preparative chromatography column 8 includes a VARIAN® Prostar™ ultra violet spectrometer.

The eluate detection device 82 is fluidly connected through a fifth liquid conduit 62 to a second liquid valve 60, which controls the flow of liquid, e.g., eluted narcotic alkaloids, into the eluate tank 56. The other end of the second liquid valve 60 is connected to a fourth liquid conduit 58, which is connected in fluid relationship to a fluid outlet 64 for the preparative chromatography column 10.

A fluid purge mechanism 39 includes a fluid purge conduit 66 that selectively allows fluid, e.g., gas or liquid, to escape from the preparative chromatography column 10. The fluid purge conduit 66 is connected to the fluid inlet 52 of the preparative chromatography column 10 through a first fluid conduit 68 that is connected in fluid relationship to a first fluid control valve 70, which controls the release of fluid, e.g., gas, from the media chamber 11 through the top portion 8 of the preparative chromatography column 10. The other end of the first fluid control valve 70 is connected to a second fluid conduit 72, which is connected in fluid relationship to the fluid purge conduit 66 for releasing fluid from the media chamber 11 when the first fluid control valve 70 is activated. Moreover, the fluid purge conduit 66 selectively allows fluid to escape from the media chamber 11 through the fluid outlet 64 of the preparative chromatography column 10 through a third fluid conduit 74 that is connected in fluid relationship to a second fluid control valve 76, which controls the release of fluid from the media chamber 11 through the bottom portion 9 of the preparative chromatography column 10. The other end of the second fluid control valve 76 is connected to a fourth fluid conduit 78 that is connected in fluid relationship to the fluid purge conduit 66 for releasing fluid from the media chamber 11 when the second fluid control valve 76 is activated.

Figure 2:
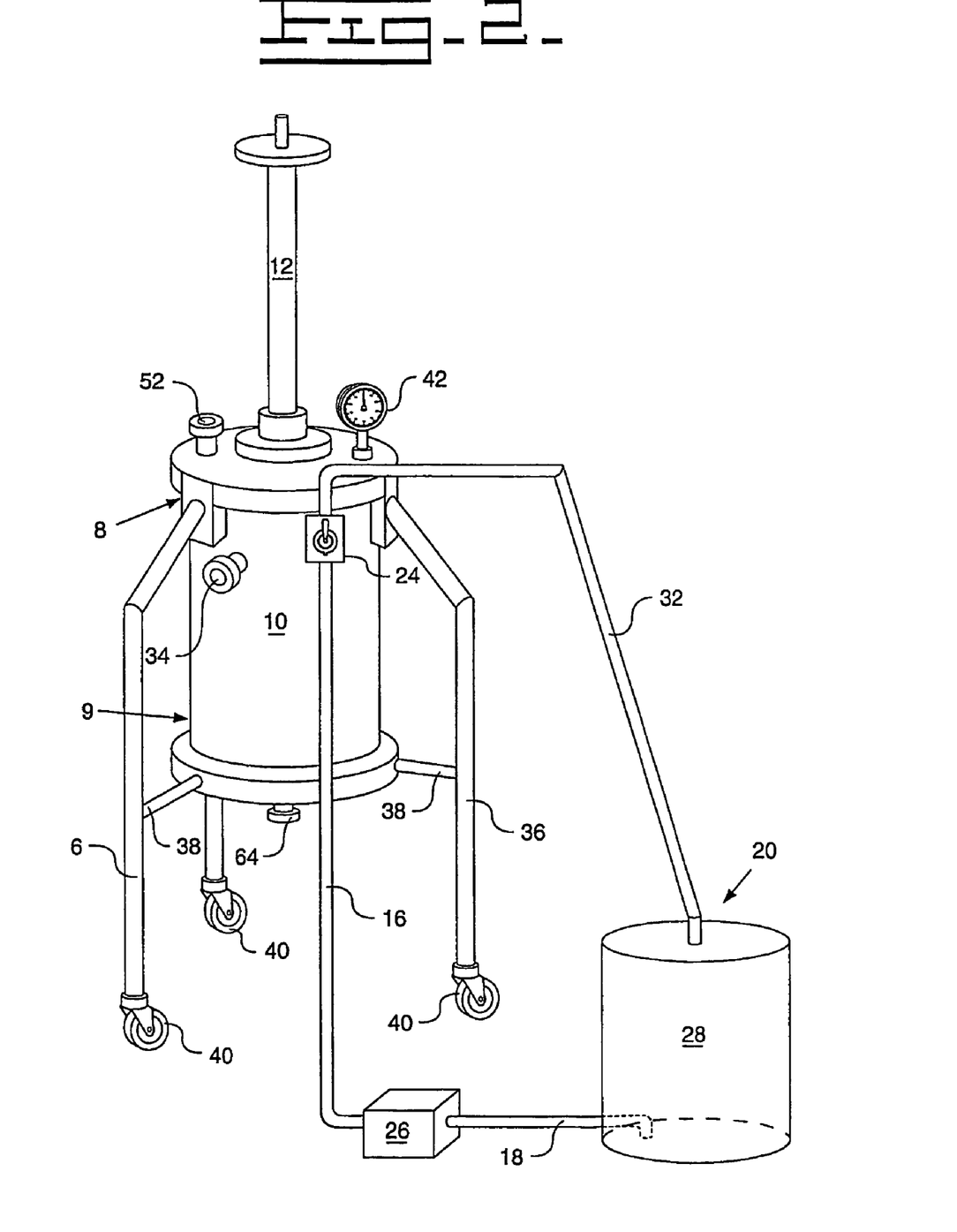
FIG. 2 is a perspective view of the preparative chromatography column of FIG. 1 for recovering a narcotic eluate from a crude alkaloid solution associated with the present invention.

As shown in FIG. 2, the preparative chromatography column 10 is supported by a series of three (3) side supports 36 that are attached at the top portion 8 of the preparative chromatography column 10. The bottom portion 9 of the preparative chromatography column 10 is attached to the three (3) side supports 36 through a series of three (3) lateral supports 38. The three (3) side supports 36 can be mounted on wheels 40. There is preferably a pressure gauge 42 that is located on top of the preparative chromatography column 10 for indicating an amount of hydraulic fluid pressure present in the hydraulic fluid chamber 15 of the preparative chromatography column 10 above the piston 12.

Figure 3:
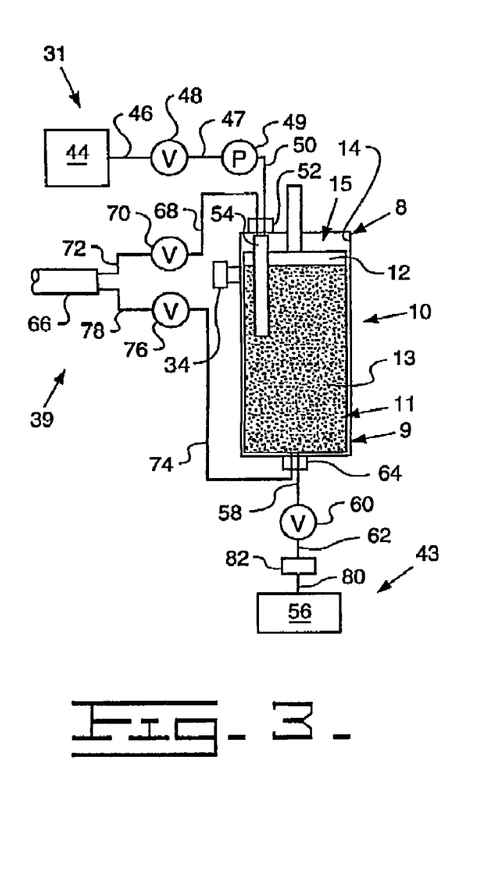
FIG. 3 is a schematic view of the preparative chromatography column and the valve mechanism of FIG. 1, wherein the preparative chromatography column has just received a transfer of stationary phase media and is releasing fluid from an inlet to the preparative chromatography column with the fluid purge mechanism.

Referring now to FIG. 3, the first step in the process is to provide stationary phase media 13 to the chromatographic column 10 through a transfer funnel 34. The stationary phase media 13 is preferably, but not necessarily, suspended in a solution to form slurry. This solution is preferably nonbuoyant so that the stationary phase media 13 will not float. An illustrative, but nonlimiting example of this type of solution may include acetonitrile. Other solutions that can be utilized may include water, methanol, ethanol and iso-propanol. Preferably, there is at least 0.255 kilograms (8.995 ounces) of stationary phase media 13.

The stationary phase media 13 is preferably hydrophobic material. This stationary phase media 13 can include silica gels, titanium oxide, zirconium oxide and polymer particles. The particles can be either porous or nonporous with a particle size that can preferably range from about 1 micrometer (39.4 microinches) to about 200 micrometers (7,874 microinches) and more preferably range from about 20 micrometers (787.4 microinches) to about 50 micrometers (1,968.5 microinches). The porous particles preferably have pores in the range of about 30 Angstroms (0.12 microinches) to about 1,000 Angstroms (3.94 microinches) with a surface area that preferably ranges from about 100 square meters/gram (3,407 square yards/ounce) to about 1,000 square meters/gram (33,488 square yard/ounce). The stationary phase media 13 may preferably include phenyl groups, cyano groups, or carbon chains (linear or branched) having two (2) to thirty (30) carbon atoms attached thereto. Reverse phase preparative chromatography operates on the basis of hydrophilicity and lipophilicity with a nonpolar stationary phase and a polar mobile phase. The greater the hydrophobic nature of the attached phenyl group, cyano group or carbon chain, the greater the tendency of the preparative chromatography column 10 to retain hydrophobic components. Thus, hydrophilic compounds elute more quickly than do hydrophobic compounds with the most polar hydrophilic components eluting first.

An optional step may include the removal of fluid, in this situation typically gas, from the media chamber 11 through the top portion 8 of preparative chromatography column 10 through the internal conduit 54 and then out the fluid inlet 52 through the first fluid conduit 68. The fluid then travels through the first fluid control valve 70 that is in an open position and then out the fluid purge conduit 66 through the second fluid conduit 72 that is connected between the first fluid control valve 70 and the fluid purge conduit 66. However, this process step can be avoided since the stationary phase media 13 must be compressed as soon as possible, i.e., within a few seconds, before the stationary phase media 13 settles out of suspension in order to avoid the creation of voids. The creation of voids will lower the efficiency of the preparative chromatography column 10.

Figure 4:
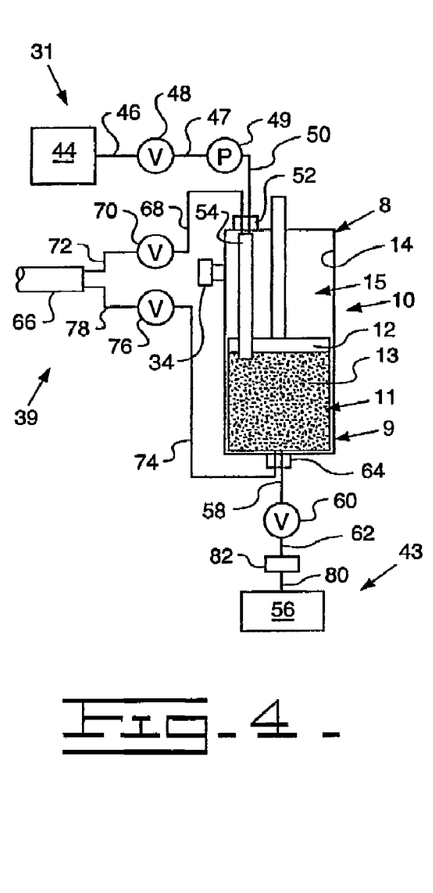
FIG. 4 is a schematic view of the preparative chromatography column and the valve mechanism, as shown in FIG. 3, that is in the process of compressing the stationary phase media and is releasing fluid from an outlet to the preparative chromatography column with the fluid purge mechanism.

The second step in the process is to compress the stationary phase media 13, which preferably, but not necessarily is in the form of slurry, to create a packed bed. This is accomplished by pumping hydraulic fluid from the hydraulic reservoir 28, as shown in FIG. 1, through the second hydraulic conduit 18 and then into the hydraulic pump 26. From the hydraulic pump 26, the hydraulic fluid is pumped out to the hydraulic switch 24 through the first hydraulic conduit 16. The hydraulic switch 24 is then opened, which allows the hydraulic fluid to flow, under pressure, into the hydraulic fluid chamber 15 of the preparative chromatography column 10 through the hydraulic inlet conduit 22. This applies pressure on the hydraulic piston 12 to depress the stationary phase media 13, as shown in FIG. 4. Initially, the hydraulic piston 12 is at the highest possible position so that the maximum volume is available within the media chamber 11. This application of pressure can vary significantly and is preferably greater than the backpressure generated by the mobile phase passing through the packed bed of stationary phase media 13. Fluid, which may be gas, nonbuoyant solvent or both, is then removed from the media chamber 11 through the bottom portion 9 of the preparative chromatography column 10 from the fluid outlet 64 through the third fluid conduit 74. The fluid then travels through the second fluid control valve 76 that is in an open position and then out the fluid purge conduit 66 through the fourth fluid conduit 78 that is connected between the second fluid control valve 76 and the fluid purge conduit 66. This results in a compressed bed of stationary phase media 13 with solvent between the particles and within the pores of the particles.

Figure 5:
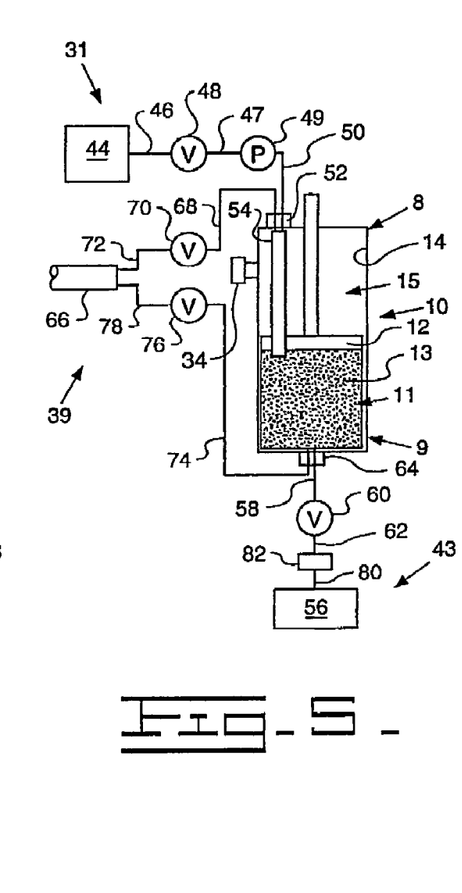
FIG. 5 is a schematic view of a preparative chromatography, as shown in FIGS. 3 and 4, that is in the process of receiving solvent into the inlet of the preparative chromatography column and eluting narcotic alkaloids from an outlet of the preparative chromatography column.

Referring now to FIG. 5, the third step in the process is to flush the solvent from the media chamber 11 of the preparative chromatography column 10 with an acidic solution. The acidic solution can include virtually any weak acid that has a pH that is in a range from about 2 to about 5. Nonlimiting examples include, but are not limited to, acetic acid, formic acid, oxalic acid, succinic acid, lactic acid and tartaric acid.

This media flushing solution, e.g., acidic solution, can be provided to the media chamber 11 through the liquid tank 44 from the previously described liquid applying mechanism 31. The media flushing solution travels from the liquid tank 44 via the first liquid conduit 46 through the open first liquid valve 48 and then into the liquid pump 49 via the second liquid conduit 47. From the liquid pump 49, the media flushing solution flows through the third liquid conduit 50 into the fluid inlet 52 of the preparative chromatography column 10 and then into the media chamber 11 through the internal conduit 54.

The fourth step in the process is to prepare an alkaloid solution from crude sources to create a salt solution. This material is mixed in an aqueous solution containing virtually any weak acid that has a pH that is in a range from about 2 to about 5. Nonlimiting examples include, but are not limited to, acetic acid, formic acid, oxalic acid, succinic acid, lactic acid and tartaric acid. This is preferably a weak organic acid, such as acetic acid but not necessarily limited thereto, with a pH that is preferably in a range from about 2 to about 5 and most preferably a pH that is from about 3 to about 4. Stronger acids such as sulfuric, hydrochloric and phosphoric might present a problem since a degradation of the thebaine present in the crude alkaloid solution could result. As with the media flushing solution, this crude alkaloid solution is then loaded into the media chamber 11 of the preparative chromatography column 10 through the liquid tank 44 from the previously described liquid applying mechanism 31. The crude alkaloid solution travels from the liquid tank 44 via the first liquid conduit 46 through the open first liquid valve 48 and then into the liquid pump 49 via the second liquid conduit 47. From the liquid pump 49, the crude alkaloid solution flows through the third liquid conduit 50 into the fluid inlet 52 of the preparative chromatography column 10 and then into the media chamber 11 through the internal conduit 54. There can be varying amounts of desired narcotic alkaloid in the crude alkaloid solution with the area percentage (area %) being defined as the area of the desired narcotic alkaloid divided by the total area of all detected components in the crude narcotic alkaloid solution. For a preparative chromatography column 10 having a minimum diameter of 5 centimeters (1.97 centimeters), there is at least 0.255 grams (0.009 ounces) of crude narcotic alkaloid solution utilized and preferably at least 6.38 grams (0.225 ounces) of crude narcotic alkaloid solution utilized and most preferably at least 8.50 grams (0.300 ounces) of crude narcotic alkaloid solution utilized.

A specific, but nonlimiting, example is the use of an alkaloid solution from crude Indian opium sources. This example is the most challenging since Indian crude is the least processed of all of the possible raw materials. The addition of a reagent is preferred to increase the thebaine purity. This was performed after the crude Indian alkaloid solution is dissolved and filtered. The reagent is believed to form an ion-pair with the acidic impurities. It is these acidic impurities that are believed to be pairing with the thebaine to inhibit recovery. When the thebaine is free from the acidic impurities, the purity of the thebaine nearly doubled with significantly less color. The reagent does not affect the elution, purity or recovery of the other desired alkaloids in the crude Indian feed. The preferred regent is triethylamine, however, several other ion-pairing agents may suffice including, but not limited to, tetrabutylammonium hydrogen sulfate, sodium dodecyl sulfate, sodium heptane sulfonate and ammonium sulfate. The concentration of the regent in the feed can range from 2.0 to 2.5 volume percent. If the reagent is less than 1.8 volume percent in the feed, then the desired thebaine purity was not achieved. If the concentration of regent exceeds 2.5 volume percent, no additional benefits are perceived. Also, the pH of the feed will typically increase as more regent, e.g., triethylamine, is added. Since the desired pH of the feed is from about 3.0 to about 3.5, the regent concentration must not increase the pH of the feed above or below this range. For example, the triethylamine concentration should preferably be in a range of 0.5 to 5.0 volume percent and more preferably not be much higher than 2.5 volume percent.

The loading ratio, which is the mass of the stationary phase media 13 divided by the mass of the crude alkaloid solution is in a range from about 1:1 to about 1:1,000 and preferably is in a range from 1:3 to 1:40 with the most preferred loading ratio being in a range from about 1:10 to 1:30. This presents a marked contrast to an analytical chromatography process, where the loading ratio of the compressed stationary phase media 13 to crude alkaloid solution is over 1:50,000.

The fifth step in the process is to feed the various mobile phases, e.g., three (3), into the preparative chromatography column 10 to receive eluates from the fluid outlet 64 of the preparative chromatography column 10. Although three (3) mobile phases are preferred for a recovery of six (6) narcotic alkaloid eluates, the present invention works just as well with a single mobile phase and the recovery of only one alkaloid eluate and all various combinations in between. The volume of mobile phase necessary to elute a narcotic alkaloid divided by the volume of mobile phase retained by the stationary phase media 13 is hereinafter defined as the dimensionless value of eluate volume, which can be applied to any size of preparative chromatography column 10.

Referring now to FIG. 5, a mobile phase can be provided to the media chamber 11 through the liquid tank 44 from the previously described liquid applying mechanism 31. As with the media flushing solution and the crude alkaloid solution, the mobile phase is then loaded into the media chamber 11 of the preparative chromatography column 10. Again, the single liquid applying mechanism 31 can be used or a separate mechanism can be used for each mobile phase. The mobile phase travels from the liquid tank 44 via the first liquid conduit 46 through the open first liquid valve 48 and then into the liquid pump 49 via the second liquid conduit 47. From the liquid pump 49, the mobile phase flows through the third liquid conduit 50 into the fluid inlet 52 of the preparative chromatography column 10 and then into the media chamber 11 through the internal conduit 54. The media chamber 11 of the preparative chromatography column 10 contains the stationary phase media 13, which is preferably, but not necessarily, compressed and the crude alkaloid solution. The alkaloids elute out the fluid outlet 64 into the fourth liquid conduit 58 and then into the second liquid valve 60. The second liquid valve 60 is opened so that eluted alkaloids can flow into a fifth liquid conduit 62 through the eluate detection device 82, e.g., a ultra violet detector, e.g., spectrometer, then into the eluate tank 56 through the sixth liquid conduit 80. There is typically at least one liter (0.264 gallons) of eluate that passes through the preparative chromatography column 10 in a single run. Since very little of the narcotic alkaloids are lost in the process, as an example, for a preparative chromatography column 10 having a minimum diameter of 5 centimeters (1.97 centimeters), there is at least 0.255 grams (0.009 ounces) of narcotic alkaloid eluted and preferably at least 6.38 grams (0.225 ounces) of narcotic alkaloid eluted and most preferably at least 8.50 grams (0.300 ounces) of narcotic alkaloid eluted.

The first mobile phase utilized is an acidic solution. Non-limiting examples of an acidic solution include, but are not limited to, acetic acid, formic acid, oxalic acid, succinic acid, lactic acid and tartaric acid with a pH that is preferably in a range from about 2 to about 5 and most preferably a pH that is from about 3 to about 4. A weak organic acid such as acetic acid is preferred since other stronger acids can degrade the thebaine present in the alkaloid solution.

The first narcotic alkaloid to elute from the preparative chromatography column 10 includes morphine. Once the morphine is removed from the preparative chromatography column 10, the morphine eluate is adjusted to a pH of 8.7 to 9.1 with a caustic solution to precipitate the morphine. This precipitated morphine is then separated from the caustic solution and washed. Separation occurs through any suitable means such as the use of a centrifuge or filter (not shown). This purification process results in a relatively high yield. As defined throughout this patent application, the yield of the narcotic alkaloid is the mass of the desired narcotic alkaloid that is removed divided by the mass of the crude alkaloid solution fed to the preparative chromatography column 10. The caustic solution preferably includes sodium hydroxide, however, a wide variety of caustic solutions may be utilized including, but not limited to, potassium hydroxide, ammonium hydroxide and carbonate salts of alkali metals. In the preferred embodiment, sodium hydroxide is present in a range from about 5 weight percent to about 50 weight percent and preferably about 25 weight percent.

It should be noted that morphine from opium can be converted into codeine. Morphine from Turkey or Australia can be used for morphine products. There is only one codeine chromatography step for a mixture of natural and synthesized codeine. The reaction step begins by dehydrating the morphine. This is accomplished by adding an organic solvent and heating to evaporate away the water. The organic solvent is preferably toluene, however, other organic solvents may suffice including ethyl acetate, chloroform, isobutanol and hexane. A methylating solution is then prepared. A nonlimiting illustration of a methylating solution includes mixing sodium ethoxide with phenyltrimethyl ammonium chloride in ethanol. The codeine molecule is essentially morphine with an additional methyl group. The methylating solution is then added gradually to the organic solvent, e.g., toluene, slurry of morphine. When the addition is completed, the reaction is quenched with water at an optimal pH of 11.5. The pH may preferably range from about 8 to about 14 and more preferably from about 11 to about 12. This forms two layers with the unreacted morphine in the bottom aqueous layer and the codeine in the upper layer with the organic solvent, e.g., toluene. The codeine-rich toluene is then extracted into an aqueous solution at a pH of 5.5. The aqueous codeine solution is then further acidified to a pH of about 3.0 to about 3.5. This is then the feed to the chromatography column 10. The unreacted morphine is then precipitated as previously described above.

There are a number of steps in an illustrative, but nonlimiting, reaction to convert morphine into codeine. An illustrative, but nonlimiting, amount would include 1 kilogram (35.27 ounces). A first step is to transfer the morphine and codeine solids to a converter vessel (not shown). A second step is to add an organic solvent, e.g., toluene. This is preferably in a range from about 5 liters (1.32 gallons) to about 50 liters (13.2 gallons) and more preferably in a range from about 9 liters (2.38 gallons) to about 11 liters (2.91 gallons) and optimally about 10 liters (2.64 gallons). A third step is to heat the contents in a range from about 100 degrees Celsius (212 degrees Fahrenheit) to about 120 degrees Celsius (248 degrees Fahrenheit) and more preferably in a range from about 105 degrees Celsius (221 degrees Fahrenheit) to about 115 degrees Celsius (239 degrees Fahrenheit) and optimally about 111 degrees Celsius (231.8 degrees Fahrenheit) to remove water with the water of hydration released at about 104 degrees Celsius (219.2 degrees Fahrenheit).

A fourth step, after the water has been removed, is to cool the contents in a range from about 85 degrees Celsius (185 degrees Fahrenheit) to about 115 degrees Celsius (239 degrees Fahrenheit) and more preferably from about 95 degrees Celsius (203 degrees Fahrenheit) to about 100 degrees Celsius (212 degrees Fahrenheit). However, temperatures higher than 100 degrees Celsius (212 degrees Fahrenheit) could cause a greater degree of evaporation.

A fifth step is to prepare a methylating solution by adding a 21 weight % solution of sodium ethoxide in ethanol in a separate vessel. The moles of sodium ethoxide added should equal the moles of morphine to be converted. For 1 kilogram (35.27 ounces) of morphine, a preferred volume of solution can range from about 0.7 liters (0.18492 gallons) to about 1.7 liters (0.45 gallons) and more preferably can range from about 1.1 liters (0.29 gallons) to about 1.4 liters (0.37 gallons) and optimally about 1.23 liters (0.33 gallons).

A sixth step is to add phenyltrimethyl ammonium chloride (aniline salt) to the sodium ethoxide. The moles added should equal the moles of morphine converted. For 1 kilogram (35.27 ounces) of morphine, a preferred amount of aniline salt to be added can range from 0.3 kilograms (10.58 ounces) to about 0.85 kilograms (29.98 ounces) and more preferably can range from about from 0.5 kilograms (17.64 ounces) to about 0.65 kilograms (22.93 ounces) and optimally about 0.57 kilograms (20.11 ounces).

A seventh step is to add additional ethanol to dissolve the salt in a preferred range from about 0.6 liters (0.16 gallons) to about 4.4 liters (1.16 gallons) and more preferably can range from about 1.2 liters (0.32 gallons) to about 2.2 liters (0.58 gallons) and is optimally about 1.5 liters (0.40 gallons).

An eighth step is to stir the solution for at least 5 minutes at room temperature, e.g., 22 degrees Celsius (72 degrees Fahrenheit). A ninth step is to add methylating solution to the morphine slurry in organic solvent, e.g., toluene, in a preferred range from about 30 to about 300 minutes and more preferably in a range from about 50 minutes to about 70 minutes. A shorter addition time can cause more impurities to form. The reaction temperature is preferably maintained in a range from about 80 degrees Celsius (176 degrees Fahrenheit) to about 120 degrees Celsius (248 degrees Fahrenheit) and more preferably in a range from about 90 degrees Celsius (194 degrees Fahrenheit) to about 100 degrees Celsius (212 degrees Fahrenheit). However, lower temperatures will not attain full conversion into codeine and higher temperatures will result in more impurity formation. The reaction slurry will eventually become a solution.

A tenth step is to add additional ethanol, after all the methylating solution has been added, to rinse the converter vessel that contained the solution, which is preferably in a range from about 100 milliliters (3.38 ounces) to about 1,500 milliliters (50.72 ounces) and more preferably in a range from about 300 milliliters (10.14 ounces) to about 400 milliliters (13.53 ounces) and is optimally about 321 milliliters (10.86 ounces). The ethanol rinse needs to be added slowly to keep the reaction temperature above 90 degrees Celsius (194 degrees Fahrenheit).

An eleventh step is to heat the reaction mixture in a range from about 95 degrees Celsius (203 degrees Fahrenheit) to about 125 degrees Celsius (257 degrees Fahrenheit) and more preferably in a range from about 105 degrees Celsius (221 degrees Fahrenheit) to about 115 degrees Celsius (239 degrees Fahrenheit) to evaporate all of the ethanol.

A twelfth step is to remove the ethanol and then the mixture is cooled to in a range from about 75 degrees Celsius (167 degrees Fahrenheit) to about 95 degrees Celsius (203 degrees Fahrenheit) and more preferably in a range from about 82 degrees Celsius (179.6 degrees Fahrenheit) to about 88 degrees Celsius (190.4 degrees Fahrenheit).

A thirteenth step is to add water to quench the reaction in a volume that is in a range from about 1.5 liters (0.40 gallons) to about 20 liters (5.28 gallons) and more preferably in a range from about 3.2 liters (0.85 gallons) to about 3.8 liters (1.00 gallons).

A fourteenth step is that the pH of the resultant of the aqueous phase is then increased above 11.5 with sodium hydroxide solution. Instead of sodium hydroxide solution, a potassium hydroxide solution, an ammonium hydroxide solution, and a wide variety of other basic solutions can be utilized.

A fifteenth step is to stir the layers for at least 10 minutes, and then the phases are given at least 5 minutes to separate. The lower aqueous phase contains unreacted morphine. The upper toluene phase contains codeine.

A sixteenth step is to drain the aqueous layer from the converter vessel. This will be then sent to a morphine precipitation vessel (not shown).

A seventeenth step is to transfer the organic solvent, e.g., toluene, layer to an extractor (not shown) and mix the organic solvent, e.g., toluene, layer with water that is preferably in a range from about 30 liters (7.93 gallons) to about 200 liters (52.83 gallons) and more preferably in a range from about 40 liters (10.57 gallons) to about 60 liters (15.85 gallons).

An eighteenth step is to adjust the pH of the aqueous layer to 5.2-5.9 with an acid, e.g., sulfuric acid, acetic acid, hydrochloric acid, and formic acid, among others. The pH range could be listed at 3.0-7.0, although a pH less than 5 will not remove a volatile impurity and a pH above 6 will not fully transfer the codeine into the aqueous layer.

A nineteenth step is to mix the layers for at least 5 minutes. After the agitation, the layers are allowed to separate for at least 5 minutes.

The aqueous layer is then sent to the chromatography column 10. More acid is then added to the aqueous layer to adjust the desired pH in a preferred range of 1.0 to 5.5 and a more preferred range of 3.0 to 3.5. This is the feed to the chromatography column 10, which is then processed as previously described. The toluene layer is sent to either hazardous waste or to a distillation column for recovery.

Utilizing the same first mobile phase, which is the above described acidic solution that is also provided by the previously described liquid applying mechanism 31, the second narcotic alkaloid to elute from the preparative chromatography column 10 is codeine.

Once the codeine is removed from the preparative chromatography column 10, then the codeine eluate is evaporated to concentrate the codeine eluate through an application of heat (not shown).

For the specific, but nonlimiting example, of attempting to separate codeine from an alkaloid solution created from very crude and unprocessed sources, e.g., Indian sources, additional process steps are preferred. In this instance, the codeine found in the Indian crude alkaloid solution is present at a low concentration and is further diluted in the chromatography process. A preferred concentration range of codeine is from about 2 grams/liter (0.267 ounces/gallon) to about 30 grams/liter (4.0 ounces/gallon) with more preferred concentration range of codeine from about 15 grams/liter liter (2.0 ounces/gallon) to about 25 grams/liter (3.34 ounces/gallon). Codeine is not fully soluble in water at a concentration above 30 grams/liter.

The codeine eluted from the crude alkaloid solution, e.g., Indian sources, has significant impurities. Preferably, the codeine fraction from Indian sources needs to be evaporated to obtain a sufficiently high enough concentration for additional processing. Direct precipitation of the codeine is not effective due to the presence of several impurities with a similar solubility. Preferably, codeine purification is achieved through liquid-liquid extraction into toluene. With two (2) extractions, the codeine is effectively transferred away from most of the colors and impurities that remain in the aqueous layer. Although only one (1) extraction or stage can be used with less codeine recovery and more than two (2) extractions or stages can be performed with little additional recovery, the preferred number of extractions or stages is two (2). The preferred organic solvent is toluene due to toluene's low solubility in water and proven performance, however, a number of other solvents may suffice including ethyl acetate, chloroform, isobutanol, and hexane. The ratio of solvent to aqueous solution is preferably in a range from 0.5 to about 3.0 and more preferably in a range from about 0.8 to about 1.2. The use of less organic solvent with a ratio lower than 0.5 would result in a need for more extractions or stages while the use of more organic solvent with a ratio more than 3.0 will dilute the codeine with little additional recovery.

A pH of 11.5 for the extraction is preferred. Although a lower pH of 10 may be suggested, the pH of at least 11.5 is preferred due to the fact that emulsion formation is essentially eliminated at this value.

The base used in the extraction is optimally 250 milligrams/milliliter (33.4 ounces/gallon) of sodium hydroxide. This can range from about 50 milligrams/milliliter milliliter (6.68 ounces/gallon) to about 750 milligrams/milliliter (100.0 ounces/gallon) with a more preferred range from about 150 milligrams/milliliter (20.0 ounces/gallon) to about 350 milligrams/milliliter (46.7 ounces/gallon).

However, other bases can be utilized such as, but not limited to, ammonium hydroxide or potassium hydroxide. Higher base concentrations will result in less pH control with the potential for overshoot and lower base concentrations can cause a greater dilution of the codeine. The stirring time for the extraction step is preferably at least one (1) minute with the longer stirring times ensuring better mass transfer and stirring times under one (1) minute creating the risk of an incomplete mass transfer. The settling time is preferably at least one (1) minute. Longer settling times may be needed depending on the amount of emulsion present. If any emulsion is present, then five (5) to ten (10) minutes may be needed to allow the layers to separate. The codeine is now in the toluene layer. This toluene is then sent to the reactor, where morphine is converted into codeine.

After the reaction is completed and the layers are separated, the codeine is then back-extracted from toluene to an aqueous layer. This is done by adding an organic acid to the extracted codeine solution in a separation vessel, which is then stirred. The preferred stirring time is at least one minute with longer times ensuring better mass transfer and shorter times running the risk of an incomplete mass transfer. The organic acid is preferably sulfuric acid, however other organic acids will suffice such as, but not limited to, acetic acid, formic acid, hydrochloric acid and phosphoric acid. The preferred number of back-extractions or stages is one (1). However, additional back-extractions or stages can be preformed with little or no additional benefit. The ratio of organic acid to aqueous solution is preferably in a range from 1.0 to about 3.0 and more preferably in a range from about 1.6 to about 2.4. The use of less organic acid with a ratio lower than 1.0 would result in diluting the codeine with little additional recovery while the use of more organic acid with a ratio more than 3.0 will create the risk of losing recovery due to the limit for the codeine solubility in the aqueous layer. The preferred pH for the back-extraction is preferably below 5.0 and more preferably under 3.5. However, if the back-extraction pH is over 3.5, there is less recovery of the codeine in the aqueous layer due to the incomplete conversion of the codeine alkaloid to the more soluble salt. The time for stirring and settling should both preferably be at least one (1) minute. Longer stirring times ensure mass transfer of the codeine. Since the layers in the back-extraction process separate rapidly, the settling time does not need to be as long as it is in the previous extraction step.

After the back-extraction, the codeine (including any codeine that was synthesized from morphine as previously described) is sent to the chromatography column 10. There it is eluted with an aqueous mobile phase. The codeine eluate is then evaporated to concentrate the codeine through an application of heat (not shown).

Once the codeine is evaporated, the codeine eluate is adjusted to a pH of over 9 and preferably a pH of over 11 with a caustic solution to precipitate the codeine. This precipitated codeine is then separated from the caustic solution and washed. Separation occurs through any suitable means such as the use of a centrifuge or filter (not shown). The caustic solution preferably includes sodium hydroxide, however, a wide variety of caustic solutions may be utilized including, but not limited to, potassium hydroxide, ammonium hydroxide and carbonate salts of alkali metals. In the preferred embodiment, sodium hydroxide is present in a range from about 5 weight percent to about 50 weight percent and preferably about 25 weight percent.

Again, utilizing the same first mobile phase, which is the above described acidic solution that is also provided by the previously described liquid applying mechanism 31, the third narcotic alkaloid to elute from the preparative chromatography column 10 is oripavine. Once the oripavine is removed from the preparative chromatography column 10, the oripavine eluate is evaporated to concentrate the oripavine eluate through an application of heat (not shown). Once the oripavine is removed from the preparative chromatography column 10, the oripavine eluate is adjusted to a pH in a range from about 8 to about 10 and preferably in a range from about 8.7 to about 9.1 with a caustic solution to precipitate the oripavine. This precipitated oripavine is then separated from the caustic solution and then washed. Separation occurs through any suitable means such as the use of a centrifuge or filter (not shown). The caustic solution preferably includes sodium hydroxide, however, a wide variety of caustic solutions may be utilized including, but not limited to, potassium hydroxide, ammonium hydroxide and carbonate salts of alkali metals. In the preferred embodiment, sodium hydroxide is present in a range from about 5 weight percent to about 50 weight percent and preferably about 25 weight percent.

The second mobile phase preferably contains a solvent. Illustrative, but nonlimiting examples, include organic solvents such as acetonitrile, and lower alkyl (C1-C5) alcohols such as methanol and isopropanol solution, which is also provided to the preparative chromatography column 10 by the previously described liquid applying mechanism 31. The second mobile phase preferably includes acetonitrile that is present in the second mobile phase in a range from about 5 volume percent to about 25 volume percent and is preferably about 10 volume percent. The second mobile phase has a pH that is preferably in a range from about 2 to about 5, which is more preferably in a range of pH from about 3 to about 4.

Utilizing this second mobile phase, the fourth narcotic alkaloid to elute from the preparative chromatography column 10 includes thebaine. Once the thebaine is removed from the preparative chromatography column 10, then the thebaine eluate is evaporated to concentrate the thebaine eluate through an application of heat (not shown).

When working with very crude sources of raw material such as that found in India, preferably but optionally, this is followed by a liquid-liquid extraction with an organic solvent. This extraction removes significant impurities and color while seemingly increasing the solubility of the thebaine alkaloid in water. A preferred concentration range of thebaine is from about 1 grams/liter (0.134 ounces/gallon) to about 8 grams/liter (1.07 ounces/gallon) with more preferred concentration range of thebaine is from about 3 grams/liter liter (0.40 ounces/gallon) to about 4 grams/liter (0.534 ounces/gallon). Higher concentrations run the risk of tar precipitations, which can trap some of the thebaine. Although only one (1) extraction or stage can be used with less thebaine recovery and more than two (2) extractions or stages can be performed with little additional recovery, the preferred number of extractions or stages is two (2). The preferred organic solvent is toluene due to toluene's low solubility in water and proven performance, however, a number of other solvents may suffice including ethyl acetate, chloroform, isobutanol and hexane. The ratio of solvent to aqueous solution is preferably in a range from 0.5 to about 3.0 and more preferably in a range from about 0.9 to about 1.2. The use of less organic solvent with a ratio lower than 0.5 would result in a need for more extractions or stages while the use of more organic solvent with a ratio more than 3.0 will dilute the thebaine with little additional recovery. The pH at which the extraction occurs is preferably in a range from about 5 to about 11 with a more preferred range from about 6 to about 7. A higher pH for extraction can cause emulsions to form and increases the settling time. The base that is added is preferably sodium hydroxide. The base used in the extraction is optimally 250 milligrams/milliliter (33.4 ounces/gallon) of sodium hydroxide. This can range from about 50 milligrams/milliliter milliliter (6.68 ounces/gallon) to about 750 milligrams/milliliter (100.0 ounces/gallon) with a more preferred range from about 150 milligrams/milliliter (20.0 ounces/gallon) to about 350 milligrams/milliliter (46.7 ounces/gallon). If higher base concentrations are used, there is less pH control making it easier to overshoot and if lower base concentrations are used, more dilution of the thebaine is the result. The setting time is preferably at least ten (10) minutes with longer settling times needed depending on the amount of emulsion that is present.

The next step is to perform a back-extraction by adding an organic acid to the extracted thebaine solution in a separation vessel, which is then stirred. The preferred stirring time is at least one minute with longer times ensuring better mass transfer and shorter times running the risk of an incomplete mass transfer. The organic acid is preferably acetic acid, however other organic acids such as, but not limited to, formic acid and oxalic acid. Mineral acid should be avoided to prevent extensive thebaine degradation. The preferred number of back-extractions or stages is one (1). However, additional back-extractions or stages can be preformed with little or no additional benefit. The ratio of organic acid to aqueous solution is preferably in a range from 1.0 to about 5.0 and more preferably in a range from about 2.0 to about 3.0. The use of less organic acid with a ratio lower than 1.0 would result in diluting the thebaine with little additional recovery while the use of more organic acid with a ratio more than 5.0 will create the risk of not fully transferring the thebaine from the organic acid, e.g., toluene, layer. The preferred pH is preferably in a range from about 2.5 to about 4.0 with a more preferred range of about 3.0 to about 3.5. A lower pH than 2.5 may cause degradation of the thebaine and a pH higher than 4.0 may create a risk of not transferring the thebaine from the layer of organic solvent, e.g., toluene. The time for stirring and the time for settling should both preferably be about one minute. Longer stirring times ensure mass transfer of the codeine. Since the layers in the back-extraction process separate rapidly, the settling time does not need to be as long as it is in the previous extraction step.

For the specific example of thebaine eluate from a very crude and unprocessed alkaloid solution, e.g., Indian sources, the addition of an organic solvent improves the thebaine purity in its precipitation. A preferred concentration range of thebaine from Indian crude alkaloid solution is from about 1 gram/liter (0.13 ounces/gallon) to about 20 grams/liter (2.67 ounces/gallon) with more preferred concentration range of thebaine from about 2 grams/liter (0.267 ounces/gallon) to about 6 grams/liter (0.80 ounces/gallon). Concentrations lower than 1 gram/liter (0.13 ounces/gallon) can result in a lower thebaine recovery while concentrations higher than 20 grams/liter (2.67 ounces/gallon) can result in less thebaine purity in the solids. The organic solvent is preferably ethanol since it minimizes the thebaine solubility in the supernatant. However, a number of alcohols will suffice such as, but not limited to, isopropanol and methanol. The organic solvent is preferably in a range from about 5 volume percent to about 20 volume percent with a more preferred range from about 8 volume percent to about 12 volume percent. A concentration of organic solvent less than 5 volume percent results in little benefit to the thebaine purity while a concentration of organic solvent of more than 20 volume percent causes more thebaine solubility and less recovery of the thebaine in the solids.

Then the thebaine eluate is adjusted to a pH that is over 9 and is preferably over 11 with a caustic solution to precipitate the thebaine. This precipitated thebaine is then separated from the caustic solution and then washed. Separation occurs through any suitable means such as the use of a centrifuge or filter (not shown). The caustic solution preferably includes sodium hydroxide, however, a wide variety of caustic solutions may be utilized including, but not limited to, potassium hydroxide, ammonium hydroxide and carbonate salts of alkali metals. In the preferred embodiment, sodium hydroxide is present in a range from about 5 weight percent to about 50 weight percent and preferably about 25 weight percent.

For the specific example of thebaine eluate from a very crude and unprocessed alkaloid solution, e.g., Indian sources, the preferred base utilized is 250 milligrams/milliliter (33.4 ounces/gallon) of sodium hydroxide. This can range from about 50 milligrams/milliliter (6.68 ounces/gallon) to about 750 milligrams/milliliter (100.0 ounces/gallon) with a more preferred range from about 150 milligrams/milliliter (20.0 ounces/gallon) to about 350 milligrams/milliliter (46.7 ounces/gallon). While, as before, a wide variety of caustic solutions may be utilized including, but not limited to, potassium hydroxide, ammonium hydroxide and carbonate salts of alkali metals. Higher concentrations of base can be utilized with the disadvantage of less pH control making it easier to overshoot and lower base concentrations may result in more dilution of the thebaine. An important aspect is to maintain the temperature of the solution during the pH adjustment. A preferred temperature range is from about 20 degrees Celsius (68 degrees Fahrenheit) to about 80 degrees Celsius (176 degrees Fahrenheit) with a more preferred range from about 50 degrees Celsius (122 degrees Fahrenheit) to about 60 degrees Celsius (140 degrees Fahrenheit). The reason that heating the thebaine solution is preferred is due to the fact that the thebaine will precipitate rapidly and will trap impurities in the solids. The more preferred temperature range from about 50 degrees Celsius (122 degrees Fahrenheit) to about 60 degrees Celsius (140 degrees Fahrenheit) is effective in preventing rapid precipitation. Temperatures above 80 degrees Celsius (176 degrees Fahrenheit) run the risk of boiling the alkaloid solution and degrading the thebaine. For the specific example of thebaine eluate from a very crude and unprocessed alkaloid solution, e.g., Indian sources, the pH is preferably over 11 to ensure solubility of the thebaine even though a lower pH of 10 or less may potentially be utilized.

After this final pH, preferably over 11, is attained, the thebaine slurry is preferably cooled to at least room temperature, which is preferably less than 25 degrees Celsius (77 degrees Fahrenheit) and above 0 degrees Celsius (32 degrees Fahrenheit). Higher temperatures over than 25 degrees Celsius (77 degrees Fahrenheit) will result in greater thebaine solubility and lower temperatures below 0 degrees Celsius (32 degrees Fahrenheit) can result in freezing the thebaine slurry.

The third mobile phase preferably contains a solvent. Illustrative, but nonlimiting examples, include organic solvents such as acetonitrile, and lower alkyl (C1-C5) alcohols such as methanol and isopropanol solution, which is also provided to the preparative chromatography column 10 by the previously described liquid applying mechanism 31. The third mobile phase preferably includes acetonitrile that is present in the third mobile phase in a range from about 15 volume percent to about 40 volume percent and more preferably is present in the third mobile phase in a range from about 15 volume percent to about 25 volume percent and is optimally present in the third mobile phase at about 20 volume percent. The third mobile phase has a pH that is preferably in a range from about 2 to about 5, which is more preferably in a range of pH from about 3 to about 4.

Utilizing this third mobile phase, the fifth narcotic alkaloid to elute from the preparative chromatography column 10 includes narcotine (noscapine). A sixth narcotic alkaloid, papaverine, may also elute. Once the narcotine is removed from the preparative chromatography column 10, then it is evaporated to concentrate the narcotine eluate through an application of heat (not shown).

In the specific, but nonlimiting, example of narcotine obtained from a crude and unprocessed alkaloid solution, e.g., Indian sources, the attempt to precipitate the concentrated narcotine fraction does not provide the requisite purity nor recovery that is desired in a commercial product. Therefore, an additional purification step of extraction into an organic solvent is utilized. Unfortunately, unlike codeine or thebaine, back-extraction results in a small, but significant yield loss. Thus, the organic solvent is evaporated away while an acidic solution is added to the extracted narcotine. The concentration of narcotine, after evaporating the chromatography fraction, is preferably in a range from about 2 grams/liter (0.267 ounces/gallon) to about 8 grams/liter (1.068 ounces/gallon) with a more preferred concentration range of narcotine from about 6 grams/liter (0.801 ounces/gallon) to about 7 grams/liter (0.935 ounces/gallon). Narcotine concentrations of over 8 grams/liter (1.068 ounces/gallon) can result in tar precipitations that can trap some of the narcotine. The preferred range of pH for the extraction is from about 3.0 to about 5.0 with a more preferred range from about 3.9 to about 4.1. If the pH is less than 3.9, more than the preferred number of extraction stages, i.e., two (2), may be required and when the pH is more than 4.1, a significant emulsion will form. The organic solvent is preferably toluene, however, a number of other organic solvents may suffice such as ethyl acetate, chloroform, isobutanol and hexane. During the extraction step, the ratio of organic solvent to aqueous solution is preferably in a range from about 0.5 to about 3.0 and more preferably in a range from about 0.9 to about 1.2. If the ratio of organic solvent to aqueous solution is less than 0.5 more extraction stages will be required and if the ratio of organic solvent to aqueous solution is greater than 3.0, the organic solvent will cause the narcotine to be diluted with very little additional recovery. The base used in the extraction is preferably 250 milligrams/milliliter (33.4 ounces/gallon) of sodium hydroxide. This can range from about 50 milligrams/milliliter (6.68 ounces/gallon) to about 750 milligrams/milliliter (100.0 ounces/gallon) with a more preferred range from about 150 milligrams/milliliter (20.0 ounces/gallon) to about 350 milligrams/milliliter (46.7 ounces/gallon). However, other bases can be utilized such as, but not limited to, ammonium hydroxide or potassium hydroxide. Higher base concentrations will result in less pH control with the potential for overshoot and lower base concentrations can cause a greater dilution of the narcotine. The stirring time for the extraction step is preferably at least one (1) minute with the longer stirring times ensuring better mass transfer and stirring times under one (1) minute creating the risk of an incomplete mass transfer. The settling time is preferably at least ten (10) minutes. Longer settling times may be needed depending on the amount of emulsion present.

The narcotine in the toluene layer is then mixed with an acidic solution that has a pH in a preferred range from about 1.0 to about 3.5. The more preferable range of pH is from about 2.5 to about 3.2. The mixture is evaporated to remove the toluene. Then the narcotine solution is adjusted to a pH that is in a range from about 3.5 to about 5.5 and preferably is in a range from about 4.0 to about 4.5 with a caustic solution to precipitate the narcotine. A preferred concentration range of narcotine from crude and unprocessed alkaloid solution, e.g., Indian sources, is from about 2 grams/liter (0.267 ounces/gallon) to about 10 grams/liter (1.34 ounces/gallon) with more preferred concentration range of narcotine from about 4 grams/liter (0.534 ounces/gallon) to about 8 grams/liter (1.07 ounces/gallon). Concentrations of narcotine higher than 10 grams/liter (1.34 ounces/gallon) will require a lower pH to ensure solubility while concentrations of narcotine lower than 2 grams/liter (0.267 ounces/gallon) will cause a lower recovery of the narcotine in the solids. The preferred range of the initial pH is from about 1.0 to about 3.0 with a more preferred range of the initial pH from about 1.6 to about 2.2. An initial pH below 1.0 will make the narcotine more soluble in solution. An initial pH above 3.0 may be utilized, however, there is the high probability that all of the narcotine will not be in solution. This will prevent all of the narcotine from being transferred to the precipitation step. Acids may be utilized to achieve this initial pH. A wide variety of acids will suffice including acetic acid or hydrochloric acid. Other organic acids or mineral acids could be used.

This precipitated narcotine is then separated from the caustic solution and then washed. Separation occurs through any suitable means such as the use of a centrifuge or filter (not shown). The caustic solution preferably includes sodium hydroxide, however, a wide variety of caustic solutions may be utilized including, but not limited to, potassium hydroxide, ammonium hydroxide and carbonate salts of alkali metals. In the preferred embodiment, sodium hydroxide is present in a range from about 5 weight percent to about 50 weight percent and preferably about 25 weight percent. Preferably, the concentration of base or caustic solution is in the range from about 100 grams/liter (13.35 ounces/gallon) to about 500 grams/liter (66.76 ounces/gallon) with more preferred concentration range of base or caustic solution from about 200 grams/liter (13.35 ounces/gallon) to about 300 grams/liter (40.06 ounces/gallon). The final pH of the solution is preferably in a range from about 4.0 to about 12.0 with a more preferred range from about 4.9 to about 5.2.

Papaverine can also be separated and purified in a similar manner if so desired. Usually, there is significant papaverine to remove from the narcotine. The removal of papaverine from narcotine is less effective when the final pH is 5.0 and above.

After this final pH is attained, the narcotine slurry is preferably cooled to at least room temperature, which is preferably less than 25 degrees Celsius (77 degrees Fahrenheit) and above 0 degrees Celsius (32 degrees Fahrenheit). Higher temperatures over 25 degrees Celsius (77 degrees Fahrenheit) will result in greater narcotine solubility and lower temperatures will provide minimum solubility and below 0 degrees Celsius (32 degrees Fahrenheit) can result in the freezing of the narcotine slurry.

The final wash or fourth mobile phase to remove any remaining coloration and other impurities from the crude alkaloid solution is preferably an organic solvent. Illustrative, but nonlimiting examples, include organic solvents such as acetonitrile, methanol and isopropanol solution. The preferred solution is a mixture containing 50 volume percent acetonitrile and 50 volume percent aqueous solution. The acetonitrile solution has a pH that is in a range from about 2 to about 5, which is preferably in a range of pH from about 3 to about 4. This is a backflow process where this final wash or fourth mobile phase is applied to the fourth liquid conduit 58 from the previously described liquid applying mechanism 31. The final wash or fourth mobile phase leaves the preparative chromatography column 10 with impurities and colorants through the internal conduit 54 and out the fluid inlet 52 and into a tank (not shown) for recovery and later potentially recycling this crude alkaloid material. This prevents the impurities and colorants from smearing the preparative chromatography column 10, which may prevent the re-use of the stationary phase media 13, which is a significant feature of this present invention.

After this final wash, the process repeats the aforementioned third, fourth and fifth process steps, which includes flushing the media chamber 11 of the preparative chromatography column 10 with an acidic solution, preparing a new alkaloid solution from crude sources and then loading this new alkaloid solution into the media chamber 11 of the preparative chromatography column 10 and then feeding the various mobile phases into the preparative chromatography column 10 to receive eluates from the fluid outlet 64 of the preparative chromatography column 10. Any narcotic alkaloids that require a second pass through the preparative chromatography column 10 is defined as a second crop with each specific type of narcotic alkaloid concentrated and purified separately.

After repeating the third, fourth and fifth process steps multiple times, the performance of the preparative chromatography column 10 will degrade from either high pressure or a loss in effectiveness in removing impurities. The stationary phase media 13 must be then removed and unpacked from the preparative chromatography column 10. This is accomplished by flipping the hydraulic switch 24 to remove the application of hydraulic fluid on the piston 12. A bottom flange (not shown) located on the bottom of the preparative chromatography column 10 is removed. A container (not shown) is placed underneath the bottom portion 9 of the preparative chromatography column 10 and the hydraulic switch is again flipped back to pump hydraulic fluid from the hydraulic reservoir 28 back into the hydraulic fluid chamber 15. This drives the piston 12 downward so that the stationary phase media 13 is pushed out of the preparative chromatography column 10 and into the container. The flange is then reattached and the piston manually lifted back up into the position shown in FIG. 3, so that the entire process can start all over again with the introduction of new stationary phase media 13 through the transfer funnel 34.

Experiments were performed with a variety of crude sources of narcotic alkaloids. Table 1, shown below, lists the crude source, the desired narcotic alkaloid, the area percentage (area %) of the crude alkaloid solution and the purified narcotic alkaloid, and the yield percentage of the purified narcotic alkaloid and percentage of color removed or purged. Table 1 demonstrates the improved purity from the crude alkaloid solution to the purified fractions of narcotic alkaloids. In some cases, additional yield for thebaine is obtained in fractions, which requires additional purification as a second crop. The yield loss for the entire process is substantially equivalent to the yield in the color purge or loss. The final wash or fourth mobile phase recovered most of the colors present in the crude alkaloid solution as well as many of the impurities.

TABLE 1

| Crude Alkaloid Source | Desired Alkaloid | Area % of Alkaloid | | % Yield of Alkaloid | |
|---|---|---|---|---|---|
| | | Crude Alkaloid Solution | Purified Alkaloid Solution | Purified Alkaloid Solution | Color Purge or Loss |
| Australian | Morphine | 96.5 | 98.8 | 99.8 | 0.2 |
| French | Morphine | 6.7 | 96.7 | 98.6 | 0.0 |
| French | Oripavine | 13.4 | 94.3 | 74.5 | 0.1 |
| French | Thebaine | 73.1 | 95.6 | 90.0 | 0.5 |
| Tasmanian | Thebaine | 95.8 | 98.4 | 90.0 | 0.5 |
| Turkish | Morphine | 89.0 | 99.2 | 98.6 | 0.1 |
| Turkish | Codeine | 5.4 | 73.9 | 95.2 | 4.8 |
| Synthetic | Codeine | 97.3 | 98.5 | 99.5 | 0.5 |
| Indian | Morphine | 9.8 | 47.5 | 95.5 | 0.0 |
| Indian | Codeine | 3.3 | 32.8 | 99.0 | 0.0 |
| Indian | Thebaine | 11.2 | 45.7 | 99.8 | 0.0 |
| Indian | Narcotine | 4.4 | 18.0 | 94.0 | 6.0 |

EXAMPLE 1

A Turkish concentrated poppy straw (CPS) was utilized as the crude source. The crude alkaloid solution that was utilized included 89.0 area % morphine, 5.4 area % codeine and 0.6 area % oripavine. The objective was to recover both morphine and codeine with high yields. The stationary phase media 13 utilized was silica with carbon eight (C8) ligands, preferably 20 micrometers (787.4 microinches) spherical particles with 120 Angstroms (0.47 microinches) pores. The details regarding the preparative chromatography column 10 utilized were previously described above. The mobile phase utilized for recovery of the morphine and codeine was an aqueous solution that included water with the addition of acetic acid to bring the pH to between 3 and 4. The removal of colors and impurities from the stationary phase media 13 was accomplished with a solution of 50% acetonitrile and 50% dilute acetic acid that has a pH of between 3 and 4. The flow direction of the initial mobile phase was from top-to-bottom while the removal of colors and impurities was accomplished from bottom-to-top (aforementioned backflow process). The results of a first trial and a second trial are detailed in Table 2 below:

TABLE 2

|  | Trial 1 | Trial 2 |
| --- | --- | --- |
| Loading ratio | 13.9 | 11.7 |
| Concentration of morphine in feed | 55.9 grams/liter (7.47 ounces/ gallon) | 39.7 grams/liter (5.30 ounces/ gallon) |
| Feed pH | 3.3 | 3.7 |
| Acid for dissolution of feed | Acetic | Acetic |
| Eluate volume prior to morphine fraction | 1.57 | 1.71 |
| Eluate volume of morphine fraction | 1.69 | 2.25 |
| Eluate volume of codeine fraction | 3.85 | 4.05 |
| Eluate volume of color fraction | 1.85 | 1.75 |
| Morphine yield in morphine fraction | 98.7% | 99.1% |
| Codeine yield in morphine fraction | 0.0% | 11.9% |
| Morphine purity in morphine fraction, area % | 98.9 | 97.6 |
| Morphine yield in codeine fraction | 1.2% | 0.9% |
| Codeine yield in codeine fraction | 92.9% | 83.9% |

The results of Trial 1 provided nearly a 99% morphine yield and with very little codeine if any. Trial 1 utilized a loading ratio of 1:13.9 for the mass of the stationary phase media 13 divided by the mass of crude alkaloid solution. In contrast, Trial 2 allowed 11.9% of the codeine to elute along with the morphine. Trial 2 utilized a loading ratio of 1:11.7 for the mass of the stationary phase media 13 divided by the mass of crude alkaloid solution, where this difference in loading ratio may have been a factor that contributed to the difference in results.

EXAMPLE 2

A Tasmanian concentrated poppy straw (CPS) was utilized as the crude source. The crude alkaloid solution that was utilized included 95.8 area % thebaine, 0.9 area % oripavine, 0.6 area % codeine and 0.4 area % 10-hydroxythebaine. The objective was to recover thebaine with a high yield and less than 0.10 area % each of oripavine, codeine, and 10-hydroxythebaine. The stationary phase media 13 utilized was silica with carbon eight (C8) ligands, preferably 20 micrometers (787.4 microinches) spherical particles with 120 Angstroms (0.47 microinches) pores. The details regarding the preparative chromatography column 10 utilized were previously described above. The mobile phase utilized for initial thebaine recovery and eluates of impurities was an aqueous solution that included water with the addition of acetic acid to bring the pH to between 3 and 4. The recovery of thebaine utilized a mobile phase that included 10-12% acetonitrile solution with an aqueous solution that includes 88-90% water. The removal of colors and impurities from the stationary phase media 13 was accomplished with a solution of 50% acetonitrile and 50% dilute acetic acid that has a pH of between 3 and 4. The flow direction of the first two mobile phases was from top-to-bottom while the removal of colors and impurities was accomplished from bottom-to-top (aforementioned backflow process). The results of a third trial and a fourth trial are detailed in Table 3 below:

TABLE 3

|  | Trial 3 | Trial 4 |
| --- | --- | --- |
| Loading ratio | 26.6 | 25.9 |
| Concentration of thebaine in feed | 27.1 grams/liter (3.62 ounces/ gallon) | 24.7 grams/liter (3.30 ounces/ gallon) |
| Feed pH | 3.8 | 3.7 |
| Acid for dissolution of feed | Acetic | Acetic |
| Eluate volume prior to thebaine fraction | 4.54 | 4.18 |
| Eluate volume of initial thebaine fraction | 0.44 | 0.22 |
| Eluate volume of thebaine fraction | 5.04 | 4.90 |
| Acetonitrile content of thebaine fraction | 7.4% | 4.7% |
| Eluate volume of color fraction | 3.76 | 3.18 |
| Thebaine yield in initial thebaine fraction | 8.3% | 4.2% |
| Thebaine yield in thebaine fraction | 90.0% | 87.4% |
| Thebaine purity in thebaine fraction, area % | 98.52 | 98.37 |
| Area % of codeine in thebaine fraction | 0.00 | 0.00 |
| Area % of oripavine in thebaine fraction | 0.00 | 0.00 |
| Area % of 10-hydroxythebaine in thebaine fraction | 0.04 | 0.28 |

The results of Trial 3 reduced the level of each impurity to under 0.10 area %. In Trial 4, the 10-hydroxythebaine remained high at 0.28%. Both Trial 3 and Trial 4 had nearly the same loading ratio of the mass of stationary phase media 13 to the mass of crude alkaloid solution; however, Trial 4 did not utilize a sufficient initial collection volume of thebaine. This fraction that contains the 10-hydroxythebaine was kept separate from other thebaine fractions due to the presence of this impurity and was purified again in a second crop recovery. Trial 4 had an initial eluate volume of 0.22 in contrast to Trial 3, which had an initial eluate volume of 0.44. Trial 3 utilized more of the acetonitrile, which allowed for a greater recovery of the thebaine.

EXAMPLE 3

An Australian concentrated poppy straw (CPS) was utilized as the crude source. The crude alkaloid solution that was utilized included 96.5 area % morphine and 2.0 area % oripavine. The objective was to recover morphine with a high yield with little or no oripavine. The stationary phase media 13 utilized was silica with carbon eight (C8) ligands, preferably 20 micrometers (787.4 microinches) spherical particles with 120 Angstroms (0.47 microinches) pores. The details regarding the preparative chromatography column 10 utilized were previously described above. The mobile phase utilized for recovery of the morphine and codeine was an aqueous solution that included water with the addition of acetic acid to bring the pH to between 3 and 4. The removal of colors and impurities from the stationary phase media 13 was accomplished with a solution of 50% acetonitrile and 50% dilute acetic acid that has a pH of between 3 and 4. The flow direction of the initial mobile phase was from top-to-bottom while the removal of colors and impurities was accomplished from bottom-to-top (aforementioned backflow process). The results of a fifth trial and a sixth trial are detailed in Table 4 below:

TABLE 4

|  | Trial 5 | Trial 6 |
|---|---|---|
| Loading ratio | 7.3 | 5.4 |
| Concentration of morphine in feed, g/l | 47.0 grams/liter (6.28 ounces/gallon) | 47.0 grams/liter (6.28 ounces/gallon) |
| Feed pH | 3.7 | 3.7 |
| Acid for dissolution of feed | Acetic | Acetic |
| Eluate volume prior to morphine fraction | 1.59 | 1.46 |
| Eluate volume of morphine fraction | 3.18 | 4.14 |
| Eluate volume of color fraction | 2.42 | 2.10 |
| Morphine yield in morphine fraction | 99.8% | 99.9% |
| Oripavine yield in morphine fraction | 0.0% | 22.5% |
| Morphine purity in morphine fraction, area % | 99.0 | 98.7 |

Trial 5 fully removed the oripavine from the morphine while Trial 6 did not completely separate the morphine from the oripavine. Trial 5 utilized a loading ratio of 1:7.3 for the mass of stationary media 13 to the mass of crude alkaloid solution. In contrast, Trial 6 utilized a loading ratio of 1:5.4 of the mass of stationary phase media 13 to the mass of crude alkaloid, where this difference in loading ratio may have been a factor that contributed to the difference in results. In both Trial 5 and Trial 6, the morphine was collected while the crude alkaloid solution was being fed into the preparative chromatography column 10. A larger eluate volume was required for Trial 6 since more volume of the crude alkaloid solution was required to be delivered to the preparative chromatography column 10. In both Trial 5 and Trial 6, there was little yield loss to the fraction of colors and impurities.

EXAMPLE 4

A French concentrated poppy straw (CPS) was utilized as the crude source. The crude alkaloid solution that was utilized included 73.1 area % thebaine, 13.4 area % oripavine, 6.7 area % morphine and 1.0 area % codeine. The objective was to recover the morphine, oripavine, and thebaine in separate fractions with high recovery and purity. The stationary phase media 13 utilized was silica with carbon eight (C8) ligands, preferably 20 micrometers (787.4 microinches) spherical particles with 120 Angstroms (0.47 microinches) pores. The details regarding the preparative chromatography column 10 utilized were previously described above. The mobile phase utilized for the morphine and oripavine recovery was an aqueous solution that included water with the addition of acetic acid to bring the pH to between 3 and 4. The recovery of thebaine utilized a mobile phase that included 10-12% acetonitrile solution with an aqueous solution that includes 88 to 90% water. The removal of colors and impurities from the stationary phase media 13 was accomplished with a solution of 50% acetonitrile and 50% dilute acetic acid that has a pH of between 3 and 4. The flow direction of the first two mobile phases was from top-to-bottom while the removal of colors and impurities was accomplished from bottom-to-top (aforementioned backflow process). The results of a seventh trial and an eighth trial are detailed in Table 5 below:

TABLE 5

|  | Trial 7 | Trial 8 |
|---|---|---|
| Loading ratio | 29.9 | 28.2 |
| Concentration of thebaine in feed | 23.7 grams/liter (3.17 ounces/gallon) | 17.3 grams/liter (2.31 ounces/gallon) |
| Feed pH | 3.8 | 3.4 |
| Acid for dissolution of feed | Acetic | Acetic |
| Eluate volume prior to morphine fraction | 1.75 | 1.72 |
| Eluate volume of morphine fraction | 0.95 | 0.88 |
| Eluate volume of morphine/codeine fraction | 0.94 | 0.58 |
| Eluate volume of oripavine fraction | 0.85 | 1.41 |
| Eluate volume of oripavine/thebaine fraction | 0.85 | 1.08 |
| Eluate volume of thebaine fraction | 8.15 | 6.22 |
| Acetonitrile content of thebaine fraction | 9.4% | 9.8% |
| Eluate volume of color fraction | 3.30 | 3.00 |
| Morphine yield in morphine fraction | 98.6% | 92.2% |
| Morphine area % in morphine fraction | 97.5 | 94.5 |
| Oripavine yield in oripavine fraction | 75.2% | 70.0% |
| Oripavine area % in oripavine fraction | 94.3 | 85.5 |
| Thebaine yield in thebaine fraction | 88.0% | 85.7% |
| Thebaine purity in thebaine fraction, area % | 95.2 | 94.6 |
| Area % of oripavine in thebaine fraction | 0.16 | 0.50 |

Both Trial 7 and Trial 8 used similar loading ratios of the mass of stationary phase media 13 to the mass of crude alkaloid solution as well as having a similar pH for the crude alkaloid solution. However, Trial 7 had better purity and yield results through the improved collection of the individual component fractions. Also, Trial 7 used a larger eluate volume to improve the morphine recovery to nearly 99%. The remaining morphine elutes with the codeine in the next fraction. Trial 7 also used a larger volume for the morphine/codeine fraction, which improved the purity of the oripavine from 85.5% area to 94.3% area. The remaining oripavine elutes with the thebaine in the oripavine/thebaine fraction, which is further purified as a second crop. Due to a delayed start in the thebaine collection, the thebaine purity is higher in Trial 7, which reduced the oripavine to under 0.2% area for this particular trial.

EXAMPLE 5

A composition of 97.3% area codeine and 0.21% area morphine was utilized as the crude source with an objective of removing colors and impurities from the codeine with a high recovery. The stationary phase media 13 utilized was silica with carbon eight (C8) ligands, preferably 50 micrometers (1968.5 microinches) spherical particles with 120 Angstroms (0.47 microinches) pores. The details regarding the preparative chromatography column 10 utilized were previously described above. The mobile phase utilized for recovery of the codeine was an aqueous solution that includes water. The removal of color from the stationary phase media 13 was accomplished with a solution of 90% methanol and 10% water. The flow direction of the initial mobile phase is from top-to-bottom while the removal of colors and impurities is accomplished from bottom-to-top (aforementioned backflow process). The results of a ninth trial and a tenth trial are detailed in Table 6 below:

TABLE 6

|  | Trial 9 | Trial 10 |
|---|---|---|
| Loading ratio | 8.6 | 10.1 |
| Concentration of codeine in feed | 23.83 grams/liter (3.18 ounces/gallon) | 16.61 grams/liter (2.22 ounces/gallon) |
| Feed pH | 3.6 | 8.5 |
| Acid for dissolution of feed | Sulfuric | Sulfuric |
| Eluate volume prior to codeine fraction | 3.4 | 4.5 |
| Eluate volume of codeine fraction | 10.0 | 9.5 |
| Eluate volume of color fraction | 4.3 | 3.6 |
| Codeine yield in codeine fraction | 98.9% | 43.6% |
| Codeine purity in codeine fraction, area % | 99.6 | 100.0 |
| Color of codeine solution* | 0.072 | 0.122 |

*Measured in a spectrophotometer at 400 nanometers (15.75 microinches) UV

With both Trial 9 and Trial 10, the codeine was synthesized from the morphine. The reaction product required additional purification, as previously described, to remove impurities and colors. Trial 9 recovered a 98.9% yield and Trial 10 recovered a 43.6% yield with both Trials using the same eluate volume. One possible reason for the lower recovery in Trial 10 was the higher pH of 8.5 for the crude alkaloid solution compared to a pH of 3.6 for the crude alkaloid solution in Trial 9. The reason for this is believed that at the higher pH, more of the codeine is present as a codeine alkaloid, which is much more strongly retained than a codeine sulfate salt.

Although the preferred embodiment of the present invention and the method of using the same has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

The invention claimed is:

1. A method for separating morphine from a crude narcotic alkaloid solution using reverse-phase preparative liquid chromatography, comprising:
    loading non-polar stationary phase media into a preparative chromatographic column;
    feeding a crude narcotic alkaloid solution that includes morphine into the preparative chromatographic column;
    applying at least one polar mobile phase to the preparative chromatographic column; and
    recovering at least one narcotic alkaloid eluate that includes morphine from the preparative chromatographic column, wherein a loading ratio of a mass of the stationary phase media to the crude narcotic alkaloid solution is in a range from about 1:1 to about 1:1000.

2. The method according to claim 1, wherein when the stationary phase media is loaded into the chromatographic column, the stationary phase media is suspended in a solution.

3. The method according to claim 2, wherein the solution is selected from the group consisting of acetonitrile, water, methanol, ethanol and iso-propanol.

4. The method according to claim 1, wherein the stationary phase media is selected from the group consisting of silica, titanium oxide, zirconium oxide and polymer particles.

5. The method according to claim 1, wherein the stationary phase media includes components selected from the group consisting of phenyl groups, cyano groups and carbon chains of two (2) to thirty (30) carbon atoms.

6. The method according to claim 4, wherein the stationary phase media includes components selected from the group consisting of phenyl groups, cyano groups and carbon chains of two (2) to thirty (30) carbon atoms.

7. The method according to claim 1, wherein the stationary phase media includes at least 0.255 kilograms (8.99 ounces) of stationary phase media.

8. The method according to claim 1, wherein the stationary phase media includes at least one particle with a size that is in a range from about 1 micrometer (39.4 microinches) to about 200 micrometers (7,874 microinches).

9. The method according to claim 1, wherein the stationary phase media includes at least one particle with a size that is in a range from about 20 micrometers (787.4 microinches) to about 50 micrometers (1,968.5 microinches).

10. The method according to claim 1, wherein the stationary phase media includes at least one particle with at least one pore, wherein the at least one pore has a size that is in a range from about 30 Angstroms (0.12 microinches) to about 1,000 Angstroms (3.94 microinches).

11. The method according to claim 1, wherein the stationary phase media includes at least one particle, wherein the at least one particle has a surface area that is in a range from about 100 square meters/gram (3,407 square yards/ounce) to about 1,000 square meters/gram (33,488 square yard/ounce).

12. The method according to claim 1, wherein after loading the stationary phase media and prior feeding a crude narcotic alkaloid solution into the chromatographic column, further includes removing fluid from the stationary phase media.

13. The method according to claim 1, wherein after loading the stationary phase media and prior to feeding a crude narcotic alkaloid solution into the chromatographic column, further includes:
    compressing the stationary phase media to create a packed bed; and
    flushing the packed bed of stationary phase media with an acidic solution.

14. The method according to claim 13, wherein the acidic solution is selected from the group consisting of acetic acid, formic acid, oxalic acid, succinic acid, lactic acid and tartaric acid.

15. The method according to claim 1, wherein the crude narcotic alkaloid solution includes crude narcotic alkaloids dissolved in an acidic solution.

16. The method according to claim 15, wherein the acidic solution is selected from the group consisting of acetic acid, formic acid, oxalic acid, succinic acid, lactic acid and tartaric acid.

17. The method according to claim 1, further includes filtering the crude narcotic alkaloid solution.

18. The method according to claim 1, further includes adding a reagent to the crude narcotic alkaloid solution.

19. The method according to claim 18, wherein the reagent is selected from the group consisting of triethylamine, tetrabutylammonium hydrogen sulfate, sodium dodecyl sulfate, sodium heptane sulfonate and ammonium sulfate.

20. The method according to claim 18, wherein the reagent is 0.5 volume percent to 5.0 volume percent of the crude narcotic alkaloid solution.

21. The method according to claim 18, wherein the reagent is 2.0 volume percent to 2.5 volume percent of the crude narcotic alkaloid solution.

22. The method according to claim 18, wherein the pH of the crude narcotic alkaloid solution is in a range from about 3.0 to about 3.5.

23. The method according to claim 1, wherein a loading ratio of a mass of the stationary phase media to the crude narcotic alkaloid solution is in a range from about 1 to 3 to about 1 to 40.

24. The method according to claim 1, wherein a loading ratio of a mass of the stationary phase media to the crude narcotic alkaloid solution is in a range from about 1 to 10 to about 1 to 30.

25. The method according to claim 1, wherein the loading of stationary phase media into the chromatographic column includes loading at least 0.255 kilograms (8.995 ounces) of the stationary phase media.

26. The method according to claim 1, wherein the feeding a crude narcotic alkaloid solution into the chromatographic column includes feeding at least 0.255 grams (0.009 ounces) of the crude narcotic alkaloid solution.

27. The method according to claim 1, wherein the feeding a crude narcotic alkaloid solution into the chromatographic column includes feeding at least 6.38 grams (0.225 ounces) of the crude narcotic alkaloid solution.

28. The method according to claim 1, wherein the feeding a crude narcotic alkaloid solution into the chromatographic column includes feeding at least 8.50 grams (0.300 ounces) of the crude narcotic alkaloid solution.

29. The method according to claim 1, wherein the recovering at least one narcotic alkaloid eluate from the chromatographic column includes recovering at least 0.255 grams (0.009 ounces) of the at least one narcotic alkaloid eluate.

30. The method according to claim 1, wherein the recovering at least one narcotic alkaloid eluate from the chromatographic column includes recovering at least 6.38 grams (0.225 ounces) of the at least one narcotic alkaloid eluate.

31. The method according to claim 1, wherein the recovering at least one narcotic alkaloid eluate from the chromatographic column includes recovering at least 8.50 grams (0.300 ounces) of the at least one narcotic alkaloid eluate.

32. The method according to claim 1, wherein the recovering at least one narcotic alkaloid eluate from the chromatographic column includes recovering at least one (1) liter (0.264 gallons) of the at least one narcotic alkaloid eluate.

33. A method for separating morphine from a crude narcotic alkaloid solution using reverse-phase preparative liquid chromatography, comprising:
   loading at least 0.255 kilograms (8.995 ounces) of non-polar stationary phase media into a preparative chromatographic column;
   feeding at least 0.255 grams (0.009 ounces) crude narcotic alkaloid solution that includes morphine into the preparative chromatographic column;
   applying at least one polar mobile phase to the preparative chromatographic column; and
   recovering at least 0.255 grams (0.009 ounces) of at least one narcotic alkaloid eluate that includes morphine from the preparative chromatographic column, wherein a loading ratio of a mass of the stationary phase media to the crude narcotic alkaloid solution is in a range from about 1:1 to about 1:1000.

34. A method for separating morphine from a crude narcotic alkaloid solution using reverse-phase preparative liquid chromatography, comprising:
   loading at least 0.255 kilograms (8.995 ounces) of non-polar stationary phase media into a preparative chromatographic column;
   feeding at least 6.38 grams (0.225 ounces) crude narcotic alkaloid solution that includes morphine into the preparative chromatographic column;
   applying at least one polar mobile phase to the preparative chromatographic column; and
   recovering at least 6.38 grams (0.225 ounces) of at least one narcotic alkaloid eluate that includes morphine from the chromatographic column, wherein a loading ratio of a mass of the stationary phase media to the crude narcotic alkaloid solution is in a range from about 1:1 to about 1:1000.

35. A method for separating morphine from a crude narcotic alkaloid solution using reverse-phase preparative liquid chromatography, comprising:
   loading at least 0.255 kilograms (8.995 ounces) of non-polar stationary phase media into a preparative chromatographic column;
   feeding at least 8.50 grams (0.300 ounces) crude narcotic alkaloid solution that includes morphine into the preparative chromatographic column;
   applying at least one polar mobile phase to the preparative chromatographic column; and
   recovering at least 8.50 grams (0.300 ounces) of at least one narcotic alkaloid eluate that includes morphine from the preparative chromatographic column, wherein a loading ratio of a mass of the stationary phase media to the crude narcotic alkaloid solution is in a range from about 1:1 to about 1:1000.

36. A method for separating morphine from a crude narcotic alkaloid solution using reverse-phase preparative liquid chromatography, comprising:
   loading at least 0.255 kilograms (8.995 ounces) of non-polar stationary phase media into a preparative chromatographic column;
   feeding at least 0.255 grams (0.009 ounces) crude narcotic alkaloid solution that includes morphine into the preparative chromatographic column;
   applying at least one polar mobile phase to the preparative chromatographic column; and
   recovering at least one (1.0) liter (0.264 gallons) of at least one narcotic alkaloid eluate that includes morphine from the preparative chromatographic column, wherein a loading ratio of a mass of the stationary phase media to the crude narcotic alkaloid solution is in a range from about 1:1 to about 1:1000.

37. The method according to claim 1, wherein the at least one mobile phase includes an acidic solution.

38. The method according to claim 37, wherein the acidic solution is selected from the group consisting of acetic acid, formic acid, oxalic acid, succinic acid, lactic acid and tartaric acid.

39. The method according to claim 37, wherein the acidic solution has a pH that is in a range from about 2 to about 5.

40. The method according to claim 37, further includes:
   adding a caustic solution to the morphine eluate to precipitate morphine; and
   separating the precipitated morphine from the caustic solution.

41. The method according to claim 40, wherein the caustic solution is selected from the group consisting of sodium hydroxide, potassium hydroxide, ammonium hydroxide and carbonate salts of alkali metals.

42. The method according to claim 40, wherein the caustic solution is added to the morphine eluate to adjust the pH in a range from about 8 to about 10.

43. A method for separating morphine from a crude narcotic alkaloid solution using reverse-phase preparative liquid chromatography, comprising:
loading non-polar stationary phase media into a preparative chromatographic column;
feeding a crude narcotic alkaloid solution that includes morphine into the preparative chromatographic column;
applying at least one polar mobile phase to the preparative chromatographic column;
recovering morphine and codeine from the preparative chromatographic column;
converting the morphine into a synthesized codeine;
feeding a synthesized codeine into the preparative chromatographic column; and
recovering the synthesized codeine from the preparative chromatographic column, wherein a loading ratio of a mass of the stationary phase media to the crude narcotic alkaloid solution is in a range from about 1:1 to about 1:1000.

44. The method according to claim 43, further includes:
adding a caustic solution to the codeine and the synthesized codeine to precipitate codeine; and
separating the precipitated codeine from the caustic solution.

45. The method according to claim 44, wherein the caustic solution is selected from the group consisting of sodium hydroxide, potassium hydroxide, ammonium hydroxide and carbonate salts of alkali metals.

46. The method according to claim 1, further includes reusing the stationary phase media after all recovering all of the narcotic eluates by driving the impurities back out of a top portion of the preparative chromatography column by applying another mobile phase to the preparative chromatography column.

47. A method for separating morphine from a crude narcotic alkaloid solution using reverse-phase preparative liquid chromatography, comprising:
feeding a crude narcotic alkaloid solution that includes morphine into a preparative chromatographic column that includes non-polar stationary phase media;
applying an acidic solution to the preparative chromatographic column;
recovering a morphine eluate, a codeine eluate and then an oripavine eluate from the preparative chromatographic column;
applying at least one organic solvent to the preparative chromatographic column; and
recovering a thebaine eluate and then a narcotine eluate from the preparative chromatographic column, wherein a loading ratio of a mass of the stationary phase media to the crude narcotic alkaloid solution is in a range from about 1:1 to about 1:1000.

48. A method for separating morphine from a crude narcotic alkaloid solution using reverse-phase preparative liquid chromatography, comprising:
feeding a crude narcotic alkaloid solution that includes morphine into a preparative chromatographic column that includes non-polar stationary phase media;
applying an acidic solution to the preparative chromatographic column, the acidic solution has a pH that is in a range from about 2 to about 5;
recovering a morphine eluate from the preparative chromatographic column;
recovering a codeine eluate from the preparative chromatographic column;
recovering an oripavine eluate from the preparative chromatographic column;
applying a first organic solvent to the preparative chromatographic column, wherein the first organic solvent has a pH that is in a range from about 2 to about 5;
recovering a thebaine eluate narcotine eluate from the preparative chromatographic column;
applying a second organic solvent to the chromatographic column, wherein the second organic solvent has a pH that is in a range from about 2 to about 5; and
recovering a narcotine eluate from the preparative chromatographic column, wherein a loading ratio of a mass of the stationary phase media to the crude narcotic alkaloid solution is in a range from about 1:1 to about 1:1000.

49. A method for separating morphine from a crude narcotic alkaloid solution using reverse-phase preparative liquid chromatography, comprising:
feeding a crude narcotic alkaloid solution that includes morphine into a chromatographic column that includes compressed non-polar stationary phase media;
applying an acidic solution to the preparative chromatographic column, wherein the acidic solution has a pH that is in a range from about 2 to about 5;
recovering a morphine eluate from the preparative chromatographic column;
adding a caustic solution to the morphine eluate to precipitate;
separating the precipitated morphine from the caustic solution;
recovering a codeine eluate from the preparative chromatographic column;
evaporating the codeine eluate to concentrate the codeine eluate;
adding a caustic solution to the concentrated codeine eluate to precipitate codeine;
separating the precipitated codeine from the caustic solution;
recovering an oripavine eluate from the preparative chromatographic column;
adding a caustic solution to the oripavine eluate to precipitate oripavine;
separating the precipitated oripavine from the caustic solution;
applying a first organic solvent to the preparative chromatographic column;
recovering a thebaine eluate narcotine eluate from the preparative chromatographic column;
evaporating the thebaine eluate, that also includes an acetate solution, to concentrate the thebaine eluate;
adding a caustic solution to the concentrated thebaine eluate to precipitate thebaine;
separating the precipitated thebaine from the caustic solution;
applying a second organic solvent to the preparative chromatographic column;
recovering a narcotine eluate from the preparative chromatographic column;
evaporating the narcotine eluate, that also includes acetate, to concentrate the narcotine eluate;
adding a caustic solution to the concentrated narcotine eluate to precipitate narcotine; and
separating the precipitated narcotine from the caustic solution, wherein a loading ratio of a mass of the stationary phase media to the crude narcotic alkaloid solution is in a range from about 1:1 to about 1:1000.

* * * * *